United States Patent
Feng et al.

(10) Patent No.: US 9,990,718 B2
(45) Date of Patent: Jun. 5, 2018

(54) SYSTEM AND METHOD FOR RECONSTRUCTING ECT IMAGE

(71) Applicant: SHANGHAI UNITED IMAGING HEALTHCARE CO., LTD., Shanghai (CN)

(72) Inventors: Tao Feng, Houston, TX (US); Wentao Zhu, Houston, TX (US); Hongdi Li, Houston, TX (US); Defu Yang, Shanghai (CN); Yun Dong, Shanghai (CN); Yang Lyu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days. days.

(21) Appl. No.: 15/450,254

(22) Filed: Mar. 6, 2017

(65) Prior Publication Data

US 2017/0249735 A1    Aug. 31, 2017

Related U.S. Application Data

(63) Continuation of application No. 15/323,077, filed as application No. PCT/CN2016/092413 on Jul. 29, 2016.

(30) Foreign Application Priority Data

Feb. 29, 2016    (CN) .......................... 2016 1 0111524

(51) Int. Cl.
*G06K 9/00* (2006.01)
*G06T 7/00* (2017.01)
(Continued)

(52) U.S. Cl.
CPC ............ *G06T 7/0012* (2013.01); *A61B 6/032* (2013.01); *A61B 6/037* (2013.01);
(Continued)

(58) Field of Classification Search
CPC ... A61B 8/5207; A61B 8/5215; A61B 8/5223; A61B 6/5294; A61B 6/5288; A61B 6/5264; A61B 6/5258
See application file for complete search history.

(56) References Cited

U.S. PATENT DOCUMENTS 8,335,363 B2 * 12/2012 Stolin .................. G06T 11/006
 382/128
9,730,664 B2 * 8/2017 Bal ..................... A61B 6/5264
(Continued)

FOREIGN PATENT DOCUMENTS

CN    101702232 A    5/2010
CN    103668465 A    3/2014
(Continued)

OTHER PUBLICATIONS

International Search Report for PCT/CN2016/092413 dated Nov. 8, 2016, 4 pages.
(Continued)

*Primary Examiner* — Avinash Yentrapati
(74) *Attorney, Agent, or Firm* — Metis IP LLC

(57) ABSTRACT

The present disclosure provides a system and method for PET image reconstruction. The method may include processes for obtaining physiological information and/or rigid motion information. The image reconstruction may be performed based on the physiological information and/or rigid motion information.

20 Claims, 25 Drawing Sheets

(51) Int. Cl.
*G06K 9/46* (2006.01)
*G06K 9/62* (2006.01)
*G06K 9/52* (2006.01)
*A61B 6/03* (2006.01)

(52) U.S. Cl.
CPC ....... *G06K 9/00335* (2013.01); *G06K 9/4671* (2013.01); *G06K 9/52* (2013.01); *G06K 9/6215* (2013.01); *G06K 9/6267* (2013.01); *G06T 2207/10072* (2013.01); *G06T 2207/20076* (2013.01); *G06T 2207/30004* (2013.01)

(56) References Cited

U.S. PATENT DOCUMENTS

| | | | |
|---|---|---|---|
| 2006/0074292 A1 | 4/2006 | Thomson et al. | |
| 2007/0040122 A1* | 2/2007 | Manjeshwar | G01T 1/2985 250/363.03 |
| 2010/0063514 A1* | 3/2010 | Maschke | A61B 5/1135 606/130 |
| 2010/0067765 A1 | 3/2010 | Buther et al. | |
| 2010/0266099 A1* | 10/2010 | Busch | A61N 5/1048 378/65 |
| 2010/0290683 A1 | 11/2010 | Demeester et al. | |
| 2010/0316275 A1* | 12/2010 | Stolin | G06T 11/006 382/131 |
| 2011/0081068 A1* | 4/2011 | Brinks | G06T 11/005 382/132 |
| 2011/0178387 A1* | 7/2011 | Ladebeck | A61B 5/055 600/411 |
| 2012/0275657 A1* | 11/2012 | Kolthammer | A61B 6/032 382/107 |
| 2013/0243331 A1 | 9/2013 | Noda et al. | |
| 2014/0119611 A1* | 5/2014 | Prevrhal | G06T 11/006 382/107 |
| 2014/0138548 A1 | 5/2014 | Li et al. | |
| 2015/0371379 A1* | 12/2015 | Averikou | A61B 8/06 382/128 |
| 2017/0164911 A1* | 6/2017 | Lv | A61B 6/037 |

FOREIGN PATENT DOCUMENTS

| | | |
|---|---|---|
| CN | 103800027 A | 5/2014 |
| CN | 103829962 A | 6/2014 |
| CN | 103845070 A | 6/2014 |
| CN | 103908278 A | 7/2014 |
| CN | 103908280 A | 7/2014 |
| CN | 103908285 A | 7/2014 |
| CN | 104068884 A | 10/2014 |
| CN | 104173070 A | 12/2014 |
| CN | 104217447 A | 12/2014 |
| CN | 104287758 A | 1/2015 |
| CN | 104346102 A | 2/2015 |
| CN | 104414671 A | 3/2015 |
| CN | 104434160 A | 3/2015 |
| CN | 103567685 B | 4/2015 |
| CN | 103767721 B | 5/2015 |
| CN | 103860187 B | 5/2015 |
| CN | 104586416 A | 5/2015 |
| CN | 104599302 A | 5/2015 |
| CN | 104665857 A | 6/2015 |
| CN | 104665858 A | 6/2015 |
| CN | 104672966 A | 6/2015 |
| CN | 103376458 B | 7/2015 |
| CN | 103800019 B | 7/2015 |
| CN | 104184473 B | 7/2015 |
| CN | 104751499 A | 7/2015 |
| CN | 104795304 A | 7/2015 |
| CN | 104840212 A | 8/2015 |
| CN | 103158203 B | 9/2015 |
| CN | 104978754 A | 10/2015 |
| CN | 105078495 A | 11/2015 |
| CN | 103376459 B | 12/2015 |
| CN | 104183012 B | 12/2015 |
| CN | 103767722 B | 4/2016 |

OTHER PUBLICATIONS

Written Opinion for PCT/CN2016/092413 dated Nov. 8, 2016, 5 pages.

* cited by examiner

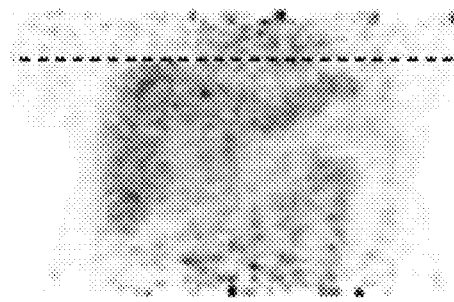 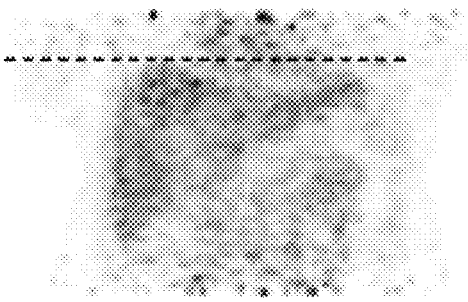
Gating Image 1　　　　　　　Gating Image 5
FIG. 18A　　　　　　　　　FIG. 18B
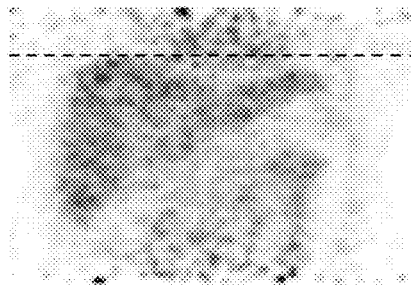 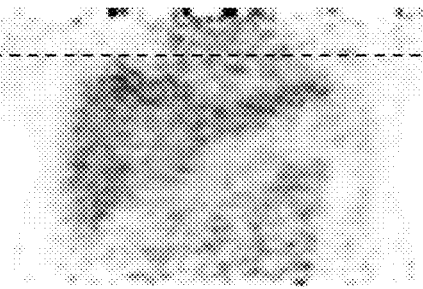
Gating Image 1　　　　　　　Gating Image 5
FIG. 18C　　　　　　　　　FIG. 18D

SYSTEM AND METHOD FOR RECONSTRUCTING ECT IMAGE

CROSS REFERENCE TO RELATED APPLICATIONS

The application is a Continuation of U.S. application Ser. No. 15/323,077, filed on Dec. 29, 2016, which is a U.S. national phase application of International Application No. PCT/CN2016/092413, filed on Jul. 29, 2016, designating the United States of America, which in turn claims priority of Chinese Patent Application No. 201610111524.7 filed on Feb. 29, 2016, the entire contents of which are hereby incorporated by reference.

TECHNICAL FIELD

This application generally relates to the field of image processing, and specifically, relates to a system and method for processing ECT motion gated image data and performing image reconstruction.

BACKGROUND

Positron emission tomography (PET) is a specialized radiology procedure that generates three-dimensional images of functional processes in a target organ or tissue of a body. Specifically, in PET studies, a biologically active molecule carrying a radioactive tracer is first introduced to a patient's body. The PET system then detects gamma rays emitted by the tracer and constructs a three-dimensional image of the tracer concentration within the body by analyzing the detected signals. Because the biologically active molecules used in PET studies are natural substrates of metabolism at the target organ or tissue, PET can evaluate the physiology (functionality) and anatomy (structure) of the target organ or tissue, as well as its biochemical properties. Changes in these properties of the target organ or tissue may provide information for the identification of the onset of a disease process before any anatomical changes relating to the disease become detectable by other diagnostic tests, such as computed tomography (CT) or magnetic resonance imaging (MRI).

Furthermore, the high sensitivity of PET—in the picomolar range—may allow the detection of small amounts of radio-labeled markers in vivo. PET may be used in conjunction with other diagnostic tests to realize simultaneous acquisition of both structural and functional information of the body. Examples include a PET/CT hybrid system, a PET/MR hybrid system.

SUMMARY

One aspect of the present disclosure relates to a method for processing ECT motion gated image data and performing image reconstruction. The method may include one or more of the following operations. The emission computed tomography (ECT) data relating to a subject may be received. A model for characterizing a physical motion may be selected. A characteristic volume of interest (VOI) of the ECT data may be determined based on the selected model. A physical motion curve may be obtained or determined based on the characteristic VOI. The ECT data may be gated based on the physical motion curve.

In a second aspect of the present disclosure, provided herein is a non-transitory computer readable medium comprising executable instructions. The instructions, when executed by at least one processor, may cause the at least one processor to effectuate a method for processing ECT motion gated image data and performing image reconstruction.

In some embodiments, the selection of a model for a physical motion may include choosing a model for a physiological motion. Further, a time of flight (TOF) probability distribution may be determined in the model for a physiological motion.

In some embodiments, the determination of the model for a physiological motion may include designating a signal quality indicator (SQI) of the physiological motion based on a VOI.

In some embodiments, the determination of a characteristic VOI may include maximizing the SQI of the physiological motion. In some embodiments, the VOI associated with maximized SQI may correspond to the characteristic VOI.

In some embodiments, the selection of a model may include selecting a physiological spectrum for the physiological motion.

In some embodiments, the determination of a physical motion may include determining movement of a center of mass of the characteristic VOI with respect to time.

In some embodiments, the ECT data may be gated based on the phase or the amplitude of the physiological motion.

In some embodiments, the selection of a model for a physical motion may include selecting a model for a rigid motion.

In some embodiments, the determination of a physical motion curve may further include one or more of the following operations. The plurality of ECT data may be divided into a plurality of subsets. A subset of the plurality of subset may be selected as a reference subset. The reference subset may be transformed into a reference representation. For each subset of the plurality of subsets except for the reference subset, the subset may be transformed into a representation, and similarity may be assessed between the representation and the reference representation.

In some embodiments, the representation or the reference representation may include an image or a histogram.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting examples, in which like reference numerals represent similar structures throughout the several views of the drawings, and wherein:

FIG. 18A through FIG. 18D provide four exemplary gated images with and/or without the process of correction according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "unit," "module," and/or "block" used herein are one method to distinguish different components, elements, parts, section or assembly of different level in ascending order. However, the terms may be displaced by other expression if they may achieve the same purpose.

It will be understood that when a unit, engine, module or block is referred to as being "on," "connected to" or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

Figure 1:
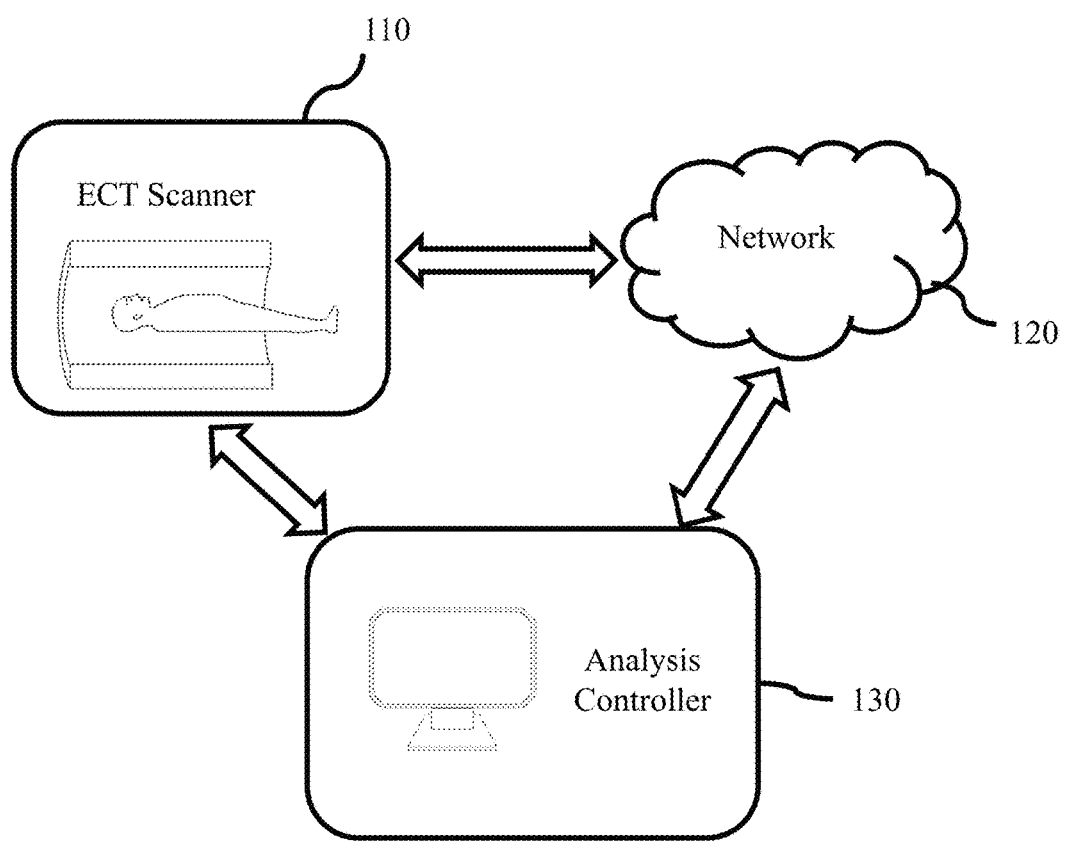
FIG. 1 illustrates a block diagram of an imaging system according to some embodiments of the present disclosure.

FIG. 1 illustrates a block diagram of an imaging system 100 according to some embodiments of the present disclosure. It should be noted that the imaging system 100 described below is merely provided for illustration purposes, and not intended to limit the scope of the present disclosure. The radiation used herein may include a particle ray, a photon ray, or the like, or any combination thereof. The particle ray may include neutron, proton, α-ray, electron, μ-meson, heavy ion, or the like, or any combination thereof. The photon beam may include X-ray, γ-ray, ultraviolet, laser, or the like, or any combination thereof. The imaging system may find its applications in different fields such as, for example, medicine or industry. Merely by way of example, the imaging system may be a positron emission tomography (PET) system, a single photon emission computed tomography (SPECT) system, a computed tomography (CT) system, a digital radiography (DR) system, a multi-modality system, or the like, or any combination thereof. Exemplary multi-modality system may include a computed tomography-positron emission tomography (CT-PET) system, a single photon emission computed tomography-magnetic resonance imaging (SPECT-MR) system, etc. As another example, the system may be used in internal inspection of components including, e.g., flaw detection, security scanning, failure analysis, metrology, assembly analysis, void analysis, wall thickness analysis, or the like, or any combination thereof.

As illustrated in FIG. 1, the imaging system 100 may include an emission computed tomography (ECT) scanner 110 and an analysis controller 130. In some embodiments, the ECT scanner 110 and the analysis controller 130 may be connected with each other via a network 120. In some embodiments, the ECT scanner 110 and the analysis controller 130 may be connected with each other directly without a network.

The ECT scanner 110 may be configured to detect radiation rays in the imaging system. In some embodiments, the ECT scanner 110 may include an SPECT scanner or a PET scanner. Take the PET for example, the PET is a specialized radiology procedure that generates and examines three-dimensional images of functional processes in a target organ or tissue of a body. Specifically, in PET studies, a biologically active molecule carrying a radioactive tracer is first introduced to the body of an object. The PET system then detects gamma rays emitted by the tracer and constructs an image of the tracer concentration within the body by analyzing the detected signal.

Merely by way of example, the radiation rays may take the form of line of response (LOR) in a PET system. Detection of the LORs may be performed by the ECT scanner 110 by way of registering coincidence events from annihilation of positrons. As another example, the radiation rays may be X-ray beams passing through an object (e.g., a patient) in a CT system. The intensity of an X-ray beam passing through the object that lies between the X-ray source and a detector (not shown) may be attenuated, and further evaluated by the ECT scanner 110. In some embodiments, the analysis controller 130 may store or access programs for imaging of various types of nuclear medicine diagnosis. Exemplary types of nuclear medicine diagnosis may include PET, SPECT, MRI, or the like, or a combination thereof. It should also be noted here that the "line of response" or "LOR" used here may be representative of a radiation ray, and not intended to limit the scope of the present disclosure. The radiation ray used herein may include a particle ray, a photon ray, or the like, or any combination thereof. The particle ray may include neutron, proton, electron, i-meson, heavy ion, or the like, or any combination thereof. For example, the radiation ray may represent the intensity of an X-ray beam passing through the subject in the case of a CT system. As another example, the radiation ray may represent the probability of a positron generated in the case of a PET system.

The analysis controller 130 may be configured to process the signals acquired by the ECT scanner 110 or retrieved from another source (for example, an imaging device, a database, storage, or the like, or a combination thereof), to reconstruct images based on the acquired signals, to control one or more parameters relating to operations performed by the ECT scanner 110. The analysis controller 130 may include a central processing unit (CPU), an application-specific integrated circuit (ASIC), an application-specific instruction-set processor (ASIP), a graphics processing unit (GPU), a physics processing unit (PPU), a microcontroller unit, a digital signal processor (DSP), a field programmable gate array (FPGA), an acorn reduced instruction set computing (RISC) machine (ARM), or the like, or any combination thereof.

For instance, the analysis controller 130 may control whether to acquire a signal, or the time when the next signal acquisition may occur. As another example, the analysis controller 130 may control which section of radiation rays may be processed during an iteration of the reconstruction. As a further example, the analysis controller 130 may control which algorithm may be selected to process the raw data of an image, and/or determine the iteration times of the iteration projection process, and/or the location of the radiation rays. In some embodiments, the analysis controller 130 may receive a real-time or a predetermined command provided by an operator including, e.g., an imaging technician, or a doctor, and adjust the ECT scanner 110. In some embodiments, the analysis controller 130 may communicate with the other modules for exchanging information relating to the operation of the scanner or other parts of the imaging system 100.

The network 120 may be a single network or a combination of different networks. For example, the network 120 may be a local area network (LAN), a wide area network (WAN), a public network, a private network, a proprietary network, a Public Telephone Switched Network (PSTN), the Internet, a wireless network, a virtual network, or any combination thereof. The network 120 may also include various network access points, for example, wired or wireless access points such as base stations or Internet exchange points (not shown in FIG. 1), through which a data source or any component of the imaging system 100 described above may connect to the network 120 in order to transmit information via the network 120.

It should be noted that the above description of the imaging system 100 is merely provided for the purposes of illustration, and not intended to limit the scope of the present disclosure. For persons having ordinary skills in the art, multiple variations and modifications may be made under the teachings of the present disclosure. For example, the assembly and/or function of the imaging system 100 may be varied or changed according to specific implementation scenarios. Merely by way of example, some other components may be added into the imaging system 100, such as a patient positioning module, a gradient amplifier module, and other devices or modules. However, those variations and modifications do not depart from the scope of the present disclosure.

Figure 2:
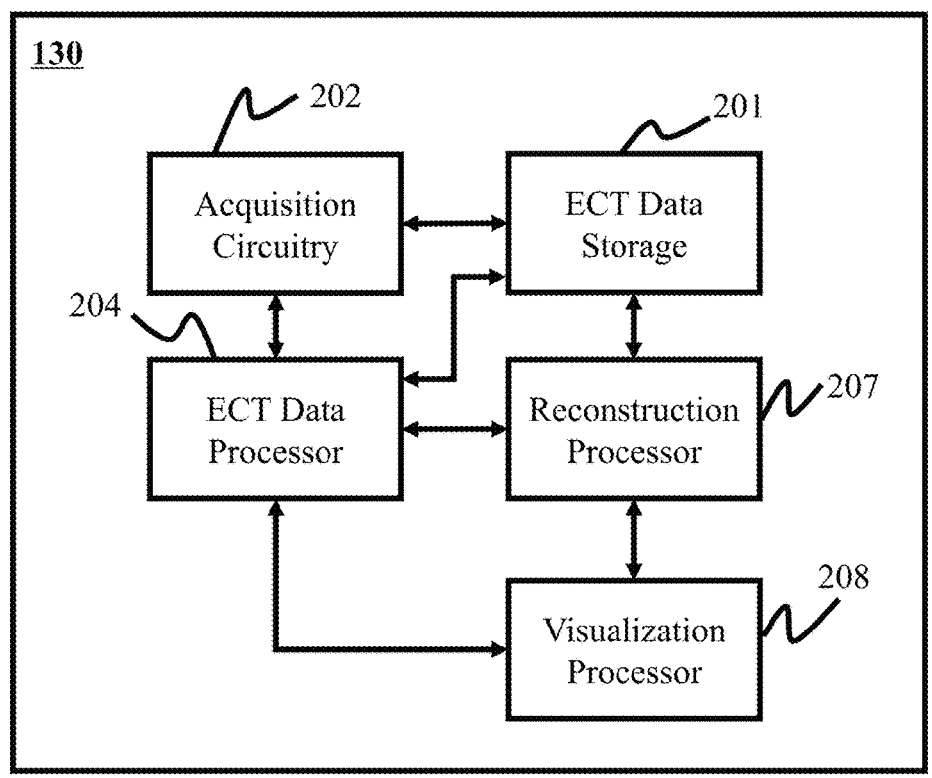
FIG. 2 is a block diagram illustrating an architecture of an analysis controller according to some embodiments of the present disclosure.

FIG. 2 is a block diagram illustrating an architecture of an analysis controller according to some embodiments of the present disclosure. The analysis controller 130 may include an ECT data storage 201, an acquisition circuitry 202, an ECT data processor 204, an image reconstruction processor 207, and/or a visualization processor 208.

The ECT data storage 201 may be used to store the acquired data or signals, control parameters, or the like. For instance, the ECT data storage 201 may store signals acquired by the ECT scanner 110. As another example, the ECT data storage 201 may store processing parameters during a process performed by the acquisition circuitry 202, the ECT processor 204, the image reconstruction processor 207, and/or the visualization processor 208. Merely by way of example, the processing parameter may include an acquisition parameter, a processing parameter (e.g., a gating parameter, a division parameter (e.g., size of a divided subset, or the like), or the like), a reconstruction algorithm, a parameter relating to visualization, or the like, or a combination thereof. In some embodiments, the ECT data storage 201 may include a random access memory (RAM), a read only memory (ROM), for example, a hard disk, a floppy disk, a cloud storage, a magnetic tape, a compact disk, a removable storage, or the like, or a combination thereof. The removable storage may read from and/or write data to a removable storage unit in a certain manner. The storage device may also be other similar means for loading computer programs or other instructions into the computer or processor.

The acquisition circuitry 202 may be configured to acquire data or signals. In some embodiments, the acquisition circuitry 202 may detect radiation rays. As described above, the acquisition circuitry 202 may be integrated in the ECT scanner 110. In some embodiments, the acquisition circuitry 202 may convert analog signals to digital signals. For example, an analog signal acquired by the ECT scanner 110 may be transmitted to the acquisition circuitry 202, and the analog signal may be converted to a corresponding digital signal. The acquisition circuitry 202 may include an amplifier, a filter, an analog-to-digital converter, or the like, or a combination thereof. In some embodiments, the acquisition circuitry 202 may receive data or signals from a related device (e.g., the ECT data storage 201, the ECT data processor 204, an external database, or the like, or a combination thereof). In some embodiments, the data or signals acquired by the acquisition circuitry 202 may be transmitted to the ECT data storage 201 and may be loaded when needed.

The ECT data processor 204 may process the ECT data. In some embodiments, the acquired data may be transmitted to the ECT data processor 204 to be further processed. In some embodiments, the ECT data processor 204 may determine a volume of interest (VOI) before processing the ECT data. As used herein, the VOI may refer to a selected subset of the data according to a particular purpose. Different VOIs may be determined under different situations. For example, a specific geometric space may be determined based on a specific VOI. As another example, a specific VOI may be selected to measure the volume of a specific tissue or tumor. As a further example, a specific VOI may be selected to reduce background noises. In some embodiments, the VOI may include a three-dimensional volume, e.g., a sphere, a column, a block, or the like, or a combination thereof. In some embodiments, the ECT data processor 204 may analyze the ECT data. For example, physical motion (e.g., physiological motion or rigid motion) related data may be obtained from the ECT data. In some embodiments, the ECT data processor 204 may process the ECT data based on an instruction or a demand from an operator (e.g., a doctor).

In some embodiments, the ECT data processor may include a division processor (not shown in FIG. 2). The division processor may be used to divide the raw ECT data (also refer to as ECT signals). The division processor may load raw ECT data from the acquisition circuitry 202 or the ECT data storage 201. In some embodiments, the raw ECT data may be divided into a plurality of subsets. For example, the division processor may divide the LORs into a plurality of groups that span, for example, approximately 100 milliseconds. For instance, the time span may be fixed and the number of LORs per group may vary. The time span may be set according to a default setting of the imaging system 100, or may be set by an operator (e.g., a doctor). As another example, the number of LORs per group may be set to be approximately 10,000, and the time span may vary. As a further example, both the number of LORs per group and the time span per group may be fixed, or one or both may be configured to be variable.

In some embodiments, the ECT data processor 204 may further include a signal filter (not shown in FIG. 2). The signal filter may remove signals within a specific frequency range from the ECT data. In some embodiments, the signal filter may remove unwanted signals within a preset frequency range (e.g., 10-100 Hz). In some embodiments, the signal filter may remove background noises. The signal filter may include a low-pass filter or a high-pass filter. A low pass filter may be a signal filter that allows passing of signal components of frequency lower than a threshold. A high pass filter may be a signal filter that allows passing of signal components of frequency higher than a threshold. The threshold may be a specific frequency or an interval of frequency. For example, the threshold may be 50 Hz. For another example, the threshold may be 100 Hz. In some embodiments, the signal filter may be integrated into any processor or unit in the analysis controller 130. In some embodiments, the signal filter is unnecessary and the filtering may be implemented via an external filter.

The image reconstruction processor 207 may reconstruct an image based on the acquired ECT data or the processed ECT data. In some embodiments, the image reconstruction processor 207 may include a microcontroller, a reduced instruction set computer (RISC), application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an acorn reduced instruction set computing (RISC) machine (ARM), or any other circuit or processor capable of executing the functions described herein, or the like, or any combination thereof. In some embodiments, the image reconstruction processor 207 may employ different kinds of imaging reconstruction techniques for the image reconstruction procedure. Exemplary image reconstruction techniques may include Fourier reconstruction, constrained image reconstruction, regularized image reconstruction in parallel MRI, or the like, or a variation thereof, or any combination thereof. In some embodiments, the image reconstruction processor 207 may use different reconstruction algorithms including an analytic reconstruction algorithm or an iterative reconstruction algorithm for the image reconstruction procedure. Exemplary analytic reconstruction algorithms may include a filter back projection (FBP) algorithm, a back projection filter (BFP) algorithm, a ρ-filtered layer gram, or the like, or a combination thereof. Exemplary iterative reconstruction algorithms may include an Maximum Likelihood Expectation Maximization (ML-EM), an Ordered Subset Expectation Maximization (OSEM), a Row-Action Maximum Likelihood Algorithm (RAMLA), a Dynamic Row-Action Maximum Likelihood Algorithm (DRAMA), or the like, or a combination thereof.

The visualization processor 208 may display imaging results generated by, for example, the image reconstruction processor 207. In some embodiments, the visualization processor 208 may include, for example, a display device and/or a user interface. Exemplary display devices may include a liquid crystal display (LCD), a light emitting diode (LED)-based display, a flat panel display or curved screen (or television), a cathode ray tube (CRT), or the like, or a combination thereof. In some embodiments, the visualization processor 208 may be connected to a device, e.g., a keyboard, a touch screen, a mouse, a remote controller, or the like, or any combination thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the visualization processor 208 is unnecessary and the imaging results may be displayed via an external device (e.g., a monitor). As a further example, the visualization processor 208 may be integrated in the image reconstruction processor 207 and the imaging results or intermediate results may be displayed in real time.

Figure 3:
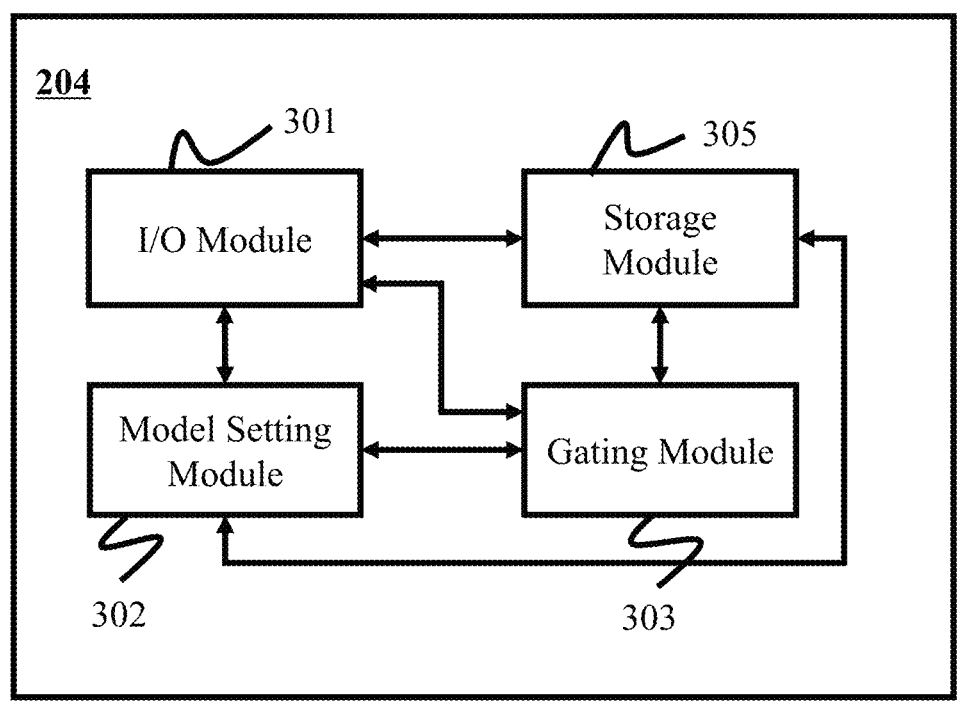
FIG. 3 is a block diagram of an architecture of an ECT data processor according to some embodiments of the present disclosure.

FIG. 3 is a block diagram of an architecture of an ECT data processor according to some embodiments of the present disclosure. The ECT data processor 204 may include an I/O module 301, a model setting module 302, a gating module 303, and a storage module 305.

The I/O module 301 may be used to input or output data or information. In some embodiments, as illustrated in FIG. 2, the acquired ECT data may be obtained via the I/O module 301. In some embodiments, the processed ECT data may be outputted via the I/O module 301. In some embodiments, the I/O module 301 may include a plate with a plurality of connecting terminals and a plurality of universal-circuits arranged on. The plurality of connecting terminals may be connected with a plurality of external devices. The universal-circuits may be used to transmit analog signals or discrete signals from/to the external devices.

The model setting module 302 may select a model and set one or more parameters relating to the model. The model may include a physiological model or a rigid motion model. In some embodiments, the ECT data may be analyzed based on the model and data of different types (e.g., physiological motion related data or rigid motion related data) may be obtained. For instance, physiological motion related data may correspond to a physiological model. In some embodiments, one or more parameters relating to the model may be set, including, VOI, probability distribution type, a signal noise ratio (SNR) calculation method, target frequency of weighted signals to be analyzed, or the like, or a combination thereof.

In some embodiments, the model setting module 302 may include a computing unit (not shown in FIG. 3) or otherwise have computation capacity. The model setting module 302 may calculate or analyze different kinds of data or information. In some embodiments, the ECT data may be analyzed based on the model, and corresponding motion related data may be classified. Merely by way of example, physiological motion related data and rigid motion related data may be obtained from the ECT data based on a physiological model and a rigid motion model, respectively. In some embodiments, the computing unit may generate a physical motion curve. As used herein, the physical motion may include a physiological motion and a rigid motion.

The gating module 303 may gate the ECT data. As used herein, "gate" may refer to that the ECT data may be classified into a plurality of groups (also referred to as "gates") and one of the groups may be selected to be further processed when needed. Merely by way of example, the ECT data may be divided into two gates, one of the gates may correspond to phase $$\frac{\pi}{2},$$

or the "peak", of physiological motion, and the other may correspond to phase $$\frac{3\pi}{2},$$

or the "valley", of physiological motion. The gating module 303 may control when or whether the gates may be transmitted to the image reconstruction processor 207 to be further processed.

The storage module 305 may be configured to store data or information generated by the I/O module 301, the model setting module 302, the computing module 303, or the control module 304. Exemplary data or information may include ECT data, models, factors of the models, control parameters, computing results, calculation algorithms, or the like, or a combination thereof. The storage module 305 may be unnecessary, any storage disclosed anywhere in the present disclosure may be used to store the data or information mentioned above. For example, the ECT data processor 204 may share a common storage with the system 100.

In some embodiments, the ECT data processor 204 may further include a control module (not shown in FIG. 3). The control module may control a parameter relating to operations performed by the model setting module 302, the storage module 305, or the like. The parameter may include an algorithm used for determining a factor of a model, a reference used for analyzing the ECT data, storage frequency, or the like, or a combination thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the storage module 305 may be integrated in any module of the ECT data processor 204. As another example, the ECT data processor 204 does not include the storage module 305, but may access and/or a storage medium of the system 100, or a storage medium external to the system 100. As a further example, the modules may be partially integrated in one or more independent modules or share one or more sub-modules. As a still further example, the I/O module 301 may be unnecessary in the ECT data processor 204, and an I/O port between any two components illustrated in FIG. 2 may be used.

Figure 4:
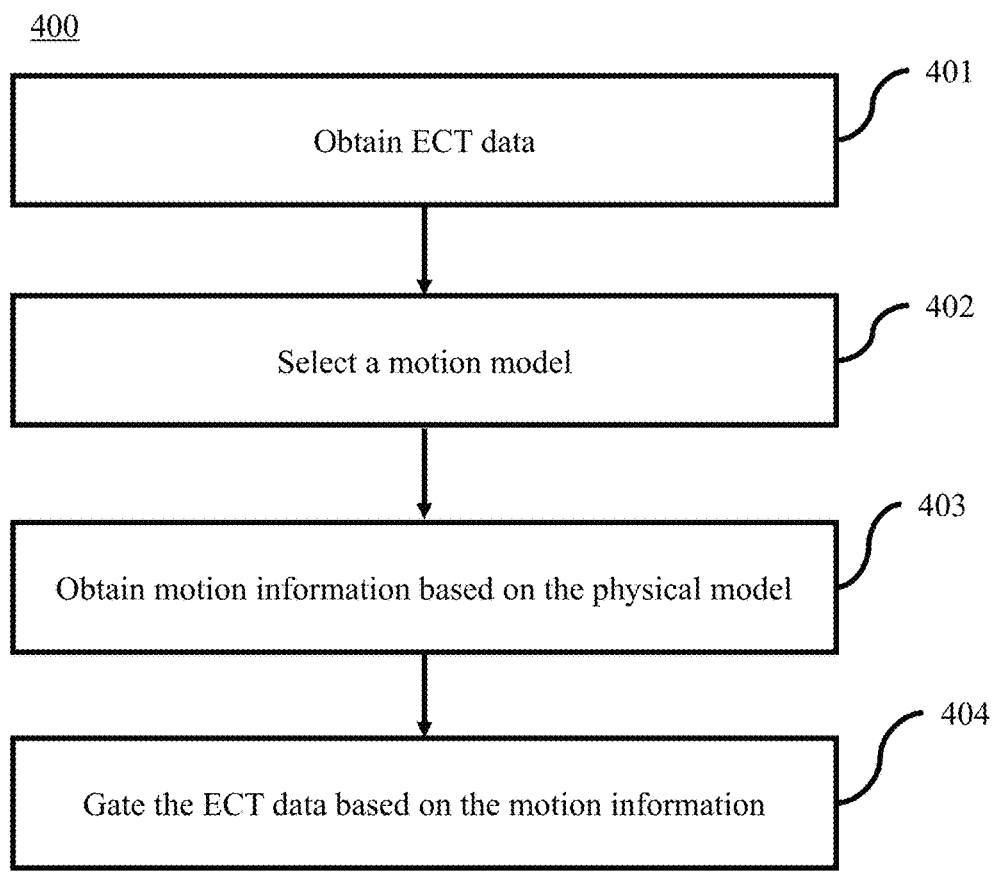
FIG. 4 is a flowchart illustrating a process for reconstructing an image according to some embodiments of the present disclosure.

FIG. 4 is a flowchart illustrating a process for reconstructing an image according to some embodiments of the present disclosure. In step 401, ECT data may be obtained. The ECT data may be obtained via the I/O module 301. The ECT data may be obtained from the acquisition circuitry 202, the ECT data storage 201, or any storage disclosed anywhere in the present disclosure. In step 402, a model may be selected for describing a corresponding physical motion. The selection may be performed by the model setting module 302. As used herein, a physical motion may include a physiological motion (e.g., respiratory motion, cardiac motion, gastrointestinal motion, or the like) and a rigid motion (e.g., body movement, or the like). The model may include a physiological model corresponding to one or more types or sources of physiological motions, a rigid motion model corresponding to one or more types or sources of rigid motions, or the like, or a combination thereof. In some embodiments, the model may be selected based on a default setting of the imaging system 100 or an instruction from an operator (e.g., a doctor).

In step 403, motion information may be obtained based on the model. The motion information may be obtained by the model setting module 302. As described in step 402, the selected model may be used for describing corresponding motion data. For instance, the distribution of the LORs may be determined based on the model, and the corresponding motion related data may be obtained. The motion information may include a physical motion curve generated based on the obtained motion data. It may be seen from the physical motion curve that the amplitudes may vary with acquisition time (see, e.g., FIG. 19A).

In step 404, the original ECT data may be gated based on the motion information. The gating may be performed by the gating module 303. A motion may occur within a specific time interval, in which the acquired ECT data may be screened out and designated as motion related data. In some embodiments, the motion related data may include physiological motion related data, rigid motion related data, or the like, or a combination thereof. In some embodiments, an amplitude threshold may be set, the amplitudes that exceed the amplitude threshold may be screened out, and the corresponding data or signals may be designated as motion related data. In some embodiments, the amplitude threshold may be set based on a default setting of the imaging system 100 or an instruction from an operator (e.g., a doctor). In some embodiments, the amplitude threshold may be adjusted under different situations. For instance, the amplitude of a respiratory motion when a subject is in a resting state may be different with the amplitude of a respiratory motion when the subject is in an exercising state.

In some embodiments, the gated ECT data may be further processed (e.g., used to reconstruct an image). An image may be reconstructed based on the gated ECT data. The image reconstruction may be performed by the image reconstruction processor 207. In some embodiments, the gated ECT data may include physiological motion related data and rigid motion related data, and images of two types may be reconstructed. In some embodiments, the gated ECT data may be corrected and motion related data may be removed or compensated before image reconstruction.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, a storing step or a caching step may be added between any two steps, in which signals or intermediate data may be stored or cached.

Figure 5:
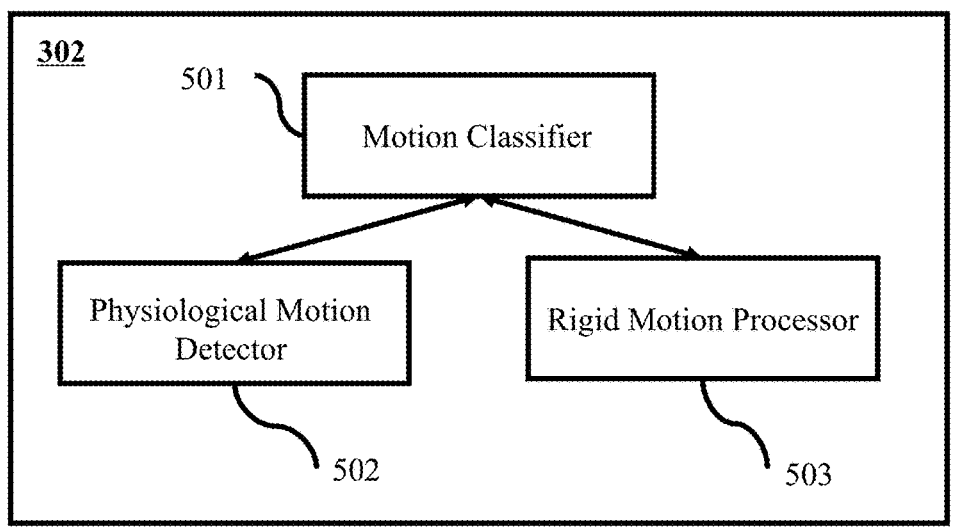
FIG. 5 illustrates an exemplary model setting module according to some embodiments of the present disclosure.

FIG. 5 illustrates an exemplary model setting module 302 according to some embodiments of the present disclosure. The model setting module 302 may include a motion classifier 501, a physiological motion detector 502, and a rigid motion processor 503.

The motion classifier 501 may classify the types of motions exhibited in the raw ECT data. In some embodiments, the motion classifier 501 may classify the motion to be of a physiological motion, a rigid motion, etc. In some embodiments, other types of motions, such as a hybrid motion, may be identified. In some embodiments, the classification may be executed based on information about a subject. For example, if the information about a subject indicates that the subject undergoes hysteria, a seizure, etc., at the time the raw ECT data are acquired, the motion classifier 501 may determine that the motion to be detected in the raw ECT data may be of a rigid motion. As another example, if the information about a subject indicates that the volume of interest of the subject lies substantially near a lung or the heart of the subject, the motion classifier 501 may determine that the motion to be detected in the raw ECT data may be a physiological motion. The result of the classification may be sent to the rigid motion processor 503 or the physiological motion detector 502 accordingly. The physiological motion detector 502 may then process the raw data to detect a physiological motion, or the rigid motion processor 503 may process the raw data to detect a rigid motion.

The exemplary detectors that may be used within the present module are not exhaustive and are not limiting. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications as falling within its scope.

Figure 6:
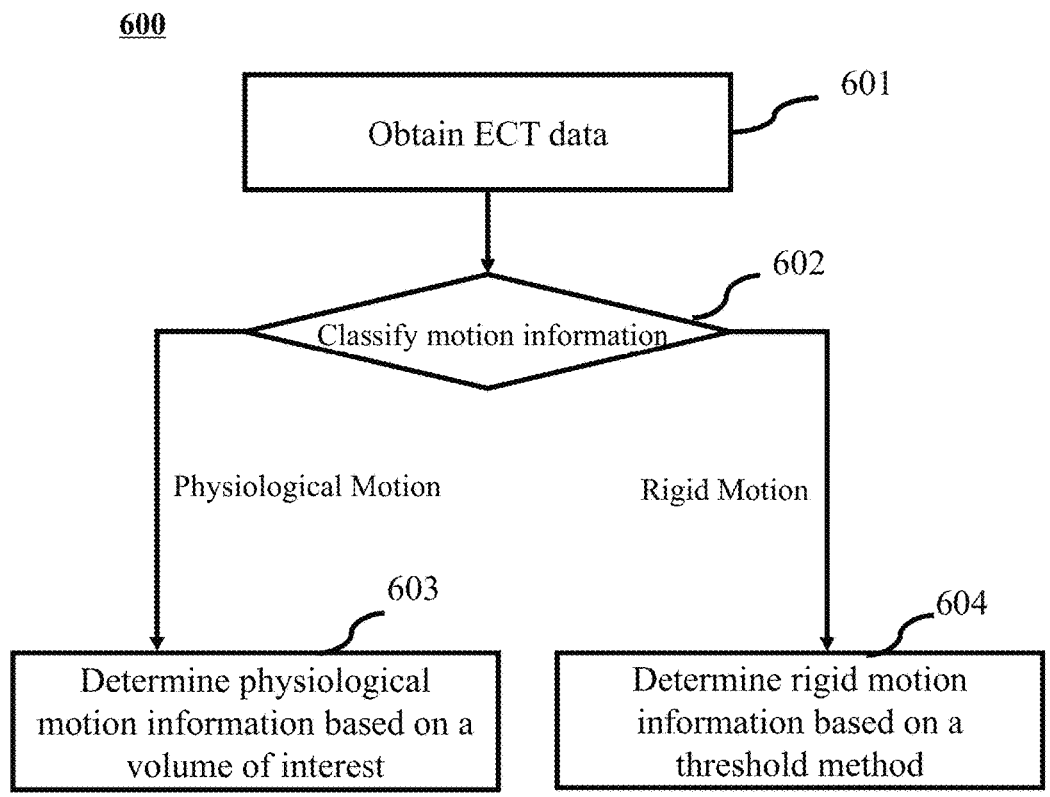
FIG. 6 is a flowchart illustrating an exemplary process for obtaining physiological motion information or rigid motion information from a set of raw ECT data according to some embodiments of the present disclosure.

FIG. 6 is a flowchart illustrating an exemplary process for obtaining physiological motion information or rigid motion information from a set of raw ECT data according to some embodiments of the present disclosure. Process 600 may be performed by processing logic including hardware (e.g., circuitry, dedicated logic, programmable logic, microcode, etc.), software (e.g., instructions run on a processing device to perform hardware simulation), or the like, or a combination thereof. In some implementations, process 600 may be performed by one or more processing devices (e.g., model setting module 302 as described in connection with FIG. 3 and FIG. 5) and elsewhere in the present disclosure.

In step 601, a set of raw ECT data may be obtained. The raw ECT data may be received from one scan systems (e.g., the ECT scanner 110 of FIG. 1), one or more storage modules 305, a storage device (e.g., a floppy disk, a hard disk, a wireless terminal, a cloud-based storage device, etc.), etc.

In step 602, an operation of classifying the type of motion in the raw ECT data may be performed. The classification may be based on the information of a subject. For example, if the information about a subject indicates that the subject undergoes hysteria, a seizure, etc., at the time the raw ECT data are acquired, the motion to be detected in the raw ECT data may be a rigid motion. As another example, if the information about a subject indicates that the volume of interest of the subject lies substantially near a lung or the heart of the subject, the motion to be detected in the raw ECT data may be a physiological motion. If the classification result is of a physiological motion type, the process may proceed to step 603; if the classification result is of a rigid motion type, the process may proceed to step 604.

In step 603, physiological motion information may be obtained from the raw ECT data. For instance, the physiological motion information may include a physiological motion curve. The physiological motion curve may show the movement of the subject with respect to time. In some embodiments, the physiological motion curve may show the movement of a certain organ including, for example, the heart, of a subject. For example, the physiological motion curve may show the movement of center of mass of a VOI of the subject. In some embodiments, the movement of the center of mass of a VOI along a certain direction, for example, the x-axis, may be obtained. The physiological motion information and/or the physiological motion curve may contain physiological information, such as the heart rate, the respiratory rate, or the like, or the combination thereof.

In some embodiments, a volume of interest may be designated first. For example, the volume of interest may be the area near the heart. As another example, the volume of interest may be the area near one or both lungs. In some embodiments, a simplified shape, such as a sphere, a cuboid, a column, a block, etc., may be used to approximate a volume of interest. A physiological motion curve may be obtained based on a volume of interest. An exemplary illustration may be seen in the process illustrated in FIG. 9 below.

In step 604, rigid motion information may be obtained from the raw ECT data. The rigid motion curve may indicate the rigid motion of a subject, for example, the movement of the head of a subject, with respect to time. A rigid motion may include translation, rotation, or the like, or a combination thereof. For example, a translation along the x-axis is an example of a rigid motion. Rigid motion may be described in terms of a motion field matrix. A motion field matrix may take the form as described in the following formula:

$$T = R_x * R_y * R_z * S \qquad \text{Formula 1}$$

where $R_x$, $R_y$, and $R_z$ may represent the rotation matrices around the x-axis, the y-axis, and the z-axis, respectively, and S may represent the translation matrix. A motion field matrix may be used to quantify the rigid motion of a subject or a portion thereof. For example, the translation along the x-axis, the y-axis, and/or the z-axis may be obtained from the translation matrix.

The rigid motion information may include a rigid motion curve. The rigid motion curve may be obtained based on a threshold. In some embodiments, a threshold may be used to determine the occurrence of a rigid motion. For example, the raw ECT data may be divided into a plurality of subsets. The similarity between two different subsets of the raw ECT data may be assessed. If the similarity between two different subsets of ECT data is smaller than the threshold, the rigid motion may be deemed to be too small to be noticed. In some embodiments, a subset of the raw ECT data may be chosen as reference ECT data. Anther subset of the raw ECT data may be considered to undergo a rigid motion if the similarity between the reference ECT data and the other subset of ECT data exceeds the threshold.

Figure 13:
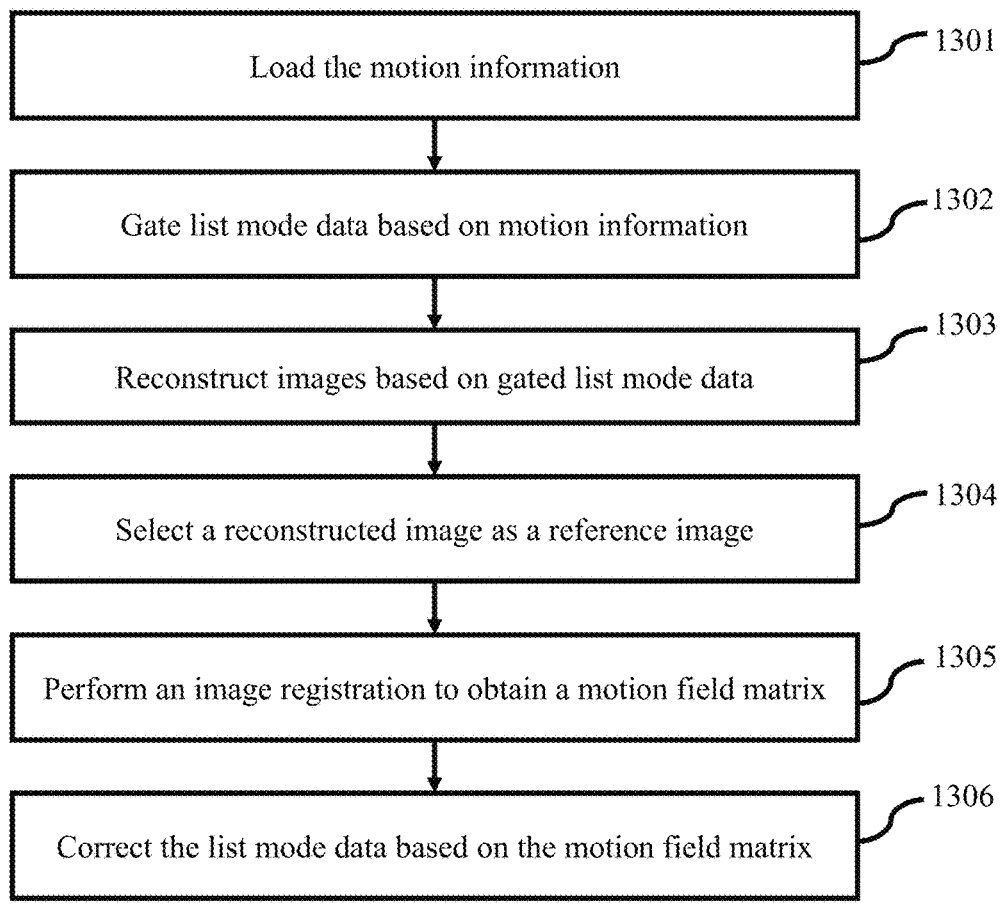
FIG. 13 is a flowchart illustrating a process for rigid motion correction according to some embodiments of the present disclosure.

In some embodiments, additional steps may be performed after step 603 or step 604. For example, a correction process may be performed on the raw ECT data based on the rigid motion curve. The spatial coordinates of the crystal pairs, used for locating the position of LORs, may be corrected by performing certain spatial transformation based on the motion field matrix. An exemplary process of correcting the list mode ECT data is illustrated in FIG. 13 and the description thereof.

Figure 7:
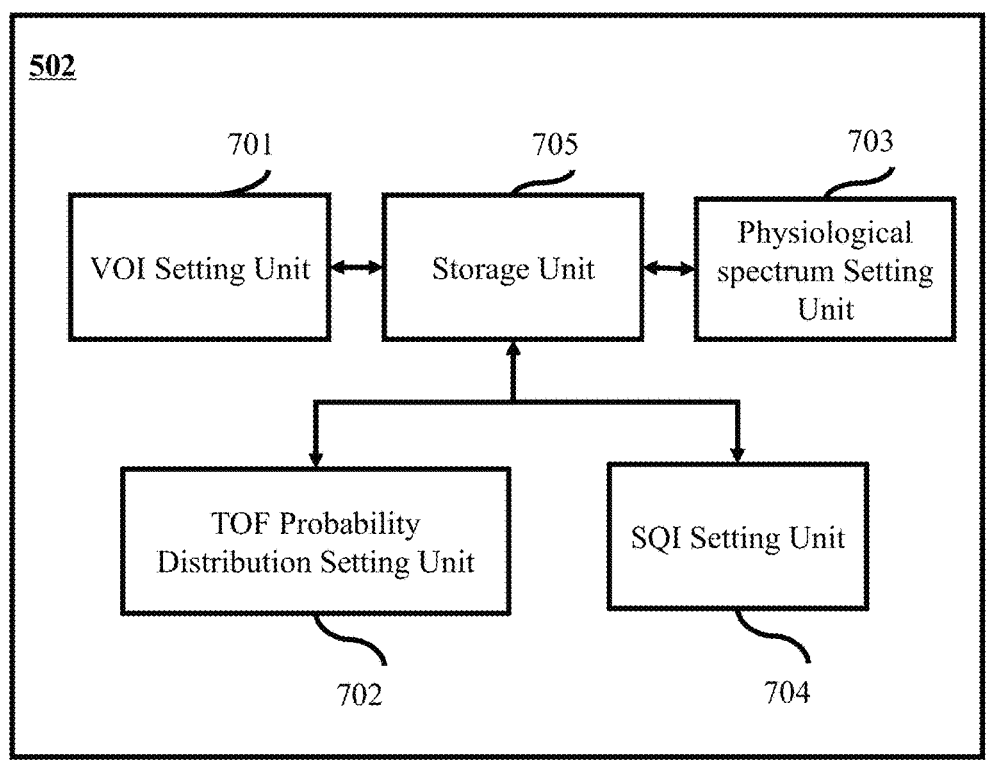
FIG. 7 illustrates an exemplary physiological motion detector according to some embodiments of the present disclosure.

FIG. 7 illustrates an exemplary physiological motion detector 502 according to some embodiments of the present disclosure. The physiological motion detector 502 may include a VOI setting unit 701, a TOF probability distribution setting unit 702, a physiological spectrum setting unit 703, a SQI setting unit 704, a storage unit 705, or the like, or a combination thereof. Other units may be included within the module, which have been omitted here in the interest of simplification.

The VOI setting unit 701 may set parameters for describing the shape of a VOI. Exemplary shapes of VOIs may be a sphere, a cuboid, a column, a block, or the like, or the combination thereof. In the exemplary embodiments that the shape of VOI is a sphere, exemplary parameters of the sphere may be (X1, X2, X3) and X4, namely the spatial coordinates of the center and the radius of the sphere, respectively. If the shape of a VOI is a block, exemplary parameters of the block may be (X1, X2, X3), X4, X5, and X6, namely the spatial coordinates of the block center, the length, the width, and the height of the block, respectively.

The TOF probability distribution setting unit 702 may set up probability models used to estimate the probabilistic distribution of list mode data, for example, the probabilistic distribution of the time of flight coordinate $\lambda_e$. See, for example, FIG. 12B and the description thereof regarding the time of flight coordinate $\lambda_e$. The probability models may be based on a Bernoulli distribution, a Poisson distribution, a uniform distribution, an exponential distribution, a normal distribution, or the like, or any combination thereof.

Figure 15:
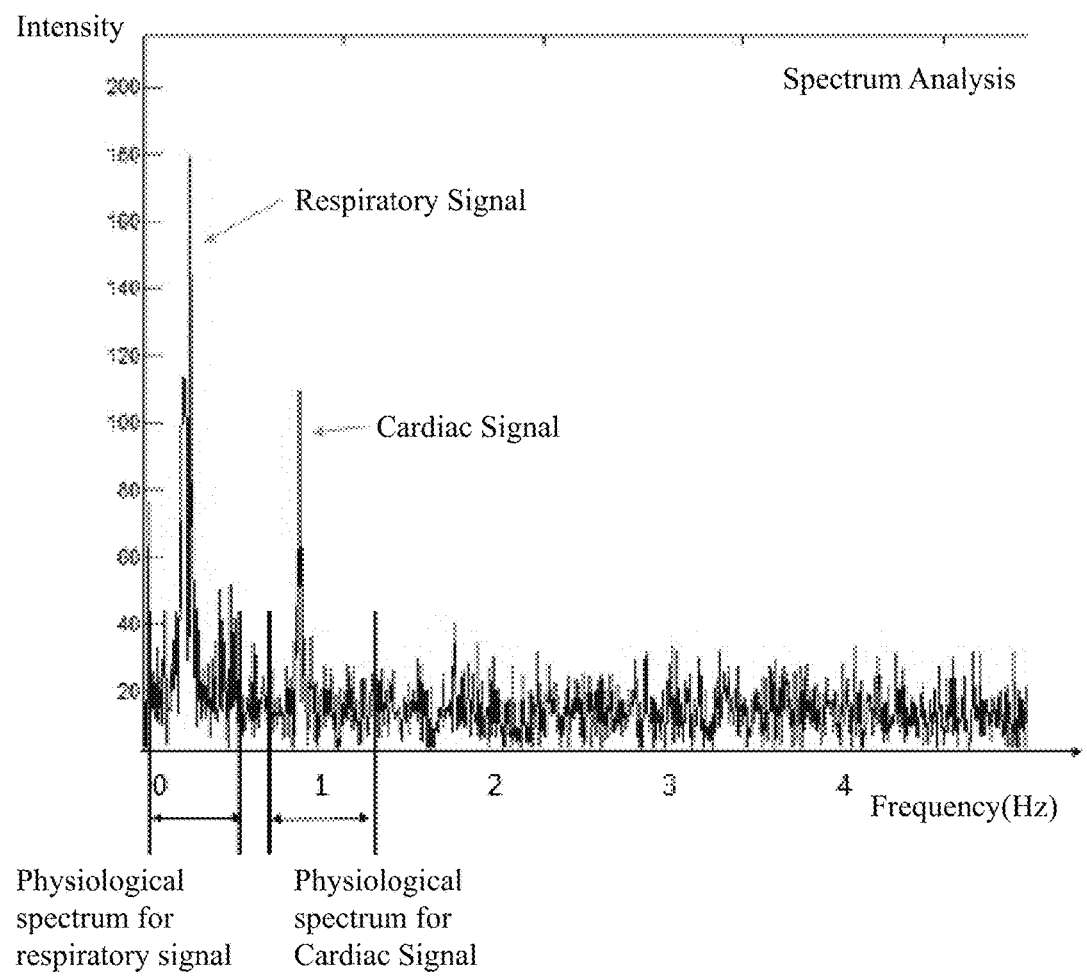
FIG. 15 provides an exemplary illustration of the physiological spectrum for a respiratory signal and a cardiac signal according to some embodiments of the present disclosure.

The physiological spectrum setting unit 703 may set a physiological spectrum for a target signal. The target signal may be a signal that contains physical motion information. For example, a target signal may be a signal that describes the movement of a center of mass of a VOI of a subject. An exemplary physiological spectrum may include the frequency range of a respiratory signal, and/or a cardiac signal, or the like, or any combination thereof. See, for example, FIG. 15 for an illustration of the physiological spectrum for a respiratory signal and a cardiac signal. Merely by way of example, the respiration rate of a human being may be 10-20 times per minute, or approximately 0.16-0.3 Hz, and thus a selection of physiological spectrum for a respiratory signal may be chosen between 0 to 0.5 Hz. As another example, the heart rate of a human being may be 50-150 times per minute, or 0.8-2.5 Hz, and thus an exemplary selection of physiological spectrum for a cardiac signal may be chosen between 0.6 to 1.5 Hz. By setting a physiological spectrum for a target signal, the physiological information contained in a target signal may be derived using a spectrum analysis approach. For example, a Fourier analysis may be used to obtain physiological information from the target signal.

The SQI setting unit 704 may calculating a signal quality indicator of a target signal with respect to a physiological spectrum. As used herein, the signal quality indicator may refer to the signal-noise-ratio, which may compare the energy level of a target signal within a physiological spectrum, to the energy level of a target signal outside of the physiological spectrum. The energy level of a signal may be measured in terms of the spectral behavior of the signal. For example, Fourier transform may be performed on the signal to obtain its spectral behavior.

The storage unit 705 may store data. The data to be stored may be from the VOI setting unit 701, the TOF probability distribution setting unit 702, the physiological spectrum setting unit 703, the SQI setting unit 704, or the like, or any combination thereof. Exemplary types of data stored may include the parameters of VOI, the probability distribution for TOF, the physiological spectrum setting, the SQI calculation method, or the like, or any combination thereof. The storage unit 705 may include a plurality of components. In some embodiments, the storage unit 705 may include a hard disk drive. In some embodiments, the storage unit 705 may include a solid-state drive. In some embodiments, the storage unit 705 may include a removable storage drive. Merely by way of examples, a non-exhaustive listing of removable storage drives that may be used in connection with the present disclosure includes a flash memory disk drive, an optical disk drive, or the like, or any combination thereof.

Figure 8:
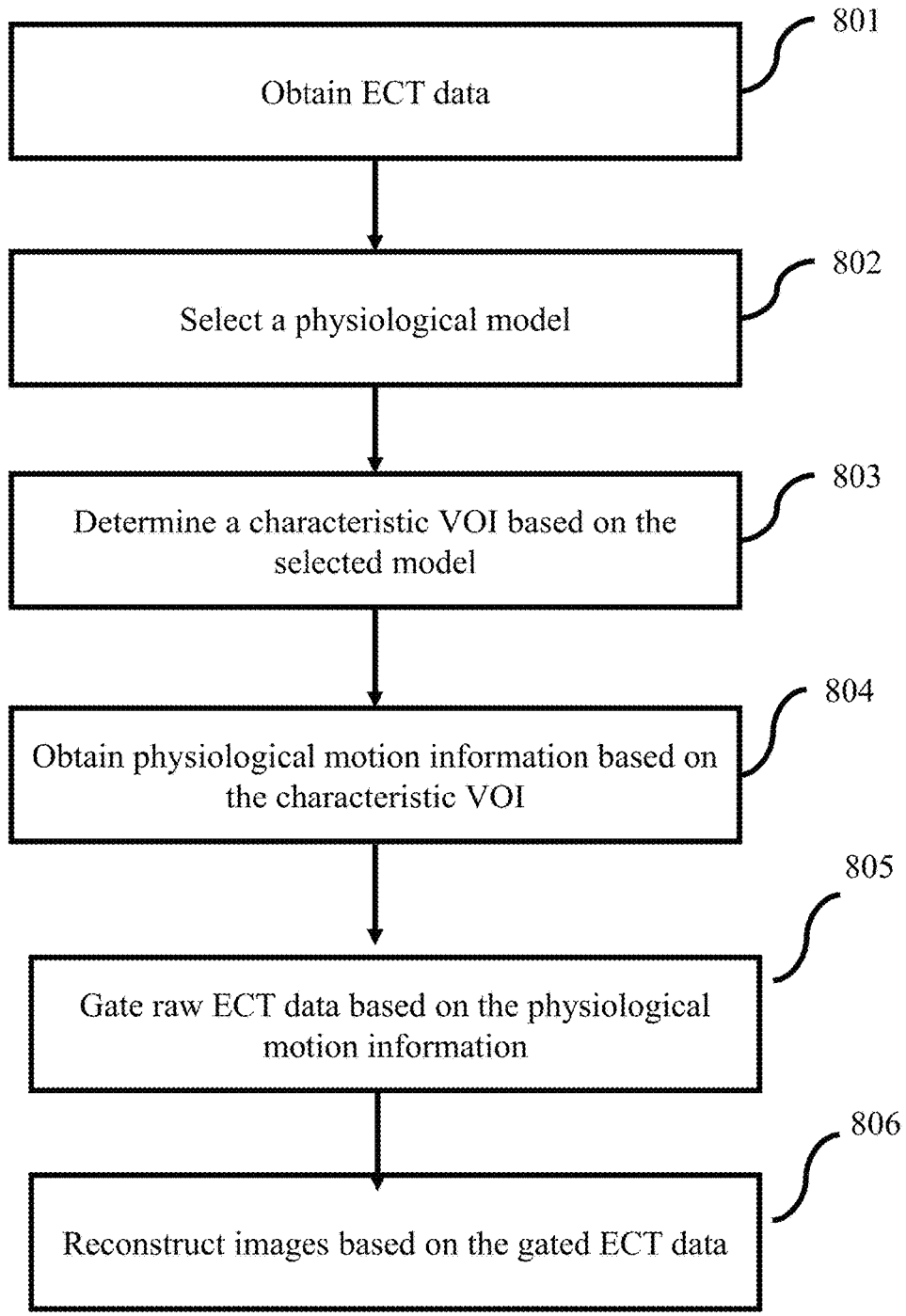
FIG. 8 is a flowchart illustrating an exemplary process for reconstructing an image by gating a set of ECT data in accordance to physiological motion information according to some embodiments of the present disclosure.

FIG. 8 is a flowchart illustrating an exemplary process for reconstructing an image by gating a set of ECT data in accordance to physiological motion information according to some embodiments of the present disclosure. Process 800 may be performed by processing logic including hardware (e.g., circuitry, dedicated logic, programmable logic, microcode, etc.), software (e.g., instructions run on a processing device to perform hardware simulation), or the like, or a combination thereof. In some implementations, process 800 may be performed by one or more processing devices (e.g., ECT data processor 204 as described in connection with FIGS. 3, 5 and 7) and elsewhere in the present disclosure.

In step 801, a set of raw ECT data may be obtained. The set of raw ECT data may refer to data from SPECT (Single-Photon Emission Computed Tomography), PET (Positron Emission Computed Tomography), etc. The set of raw ECT data may be obtained by scanning a target body, or from a storage unit, or some database via a network. The set of raw ECT data may be stamped with time information and spatial information of an annihilation event. In some embodiments, the set of ECT data may refer to list mode data. In some embodiments, the set of ECT data may refer to sinogram data. The sinogram data may be stamped with time information, and/or spatial information, or any other information that may be familiar to a person of ordinary skill in the art.

In step 802, a physiological model may be selected. The physiological model may be a method to process raw ECT data to obtain physiological information. For example, the model may include specifying the shape of VOI, setting parameters such as spatial coordinates for a VOI, designating a TOF probability distribution type, a SQI calculation method, a physiological spectrum for a target signal, or the like, or any combination thereof. Model selection may be accomplished in the model setting module 302.

Figure 16A:
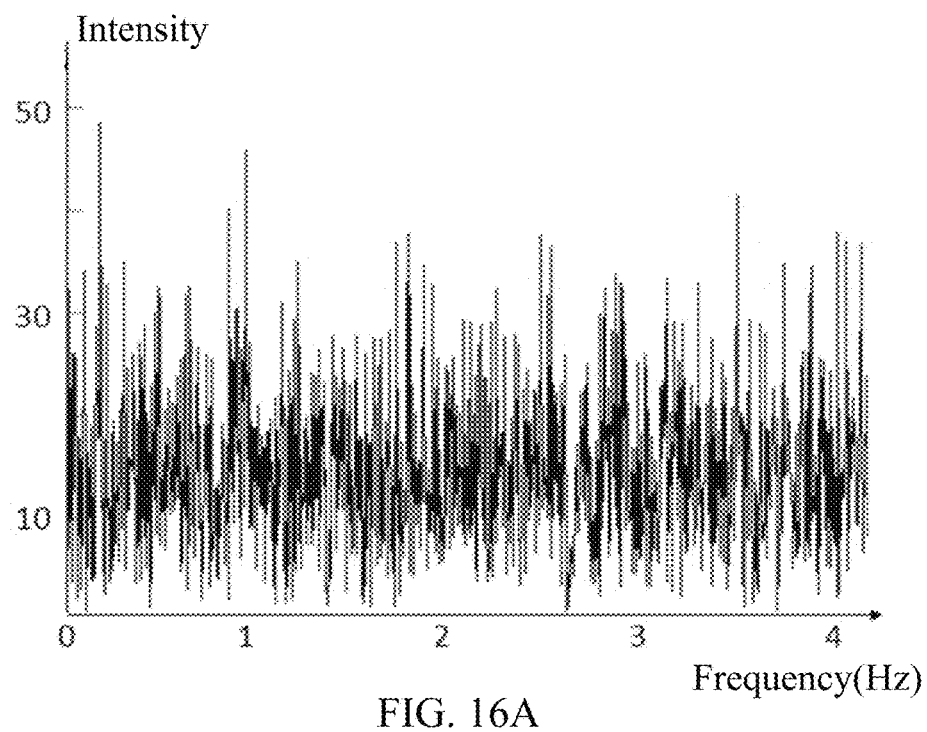
FIG. 16A illustrates the spectrum analysis of a weighted signal without reference to a characteristic VOI according to some embodiments of the present disclosure.
Figure 16B:
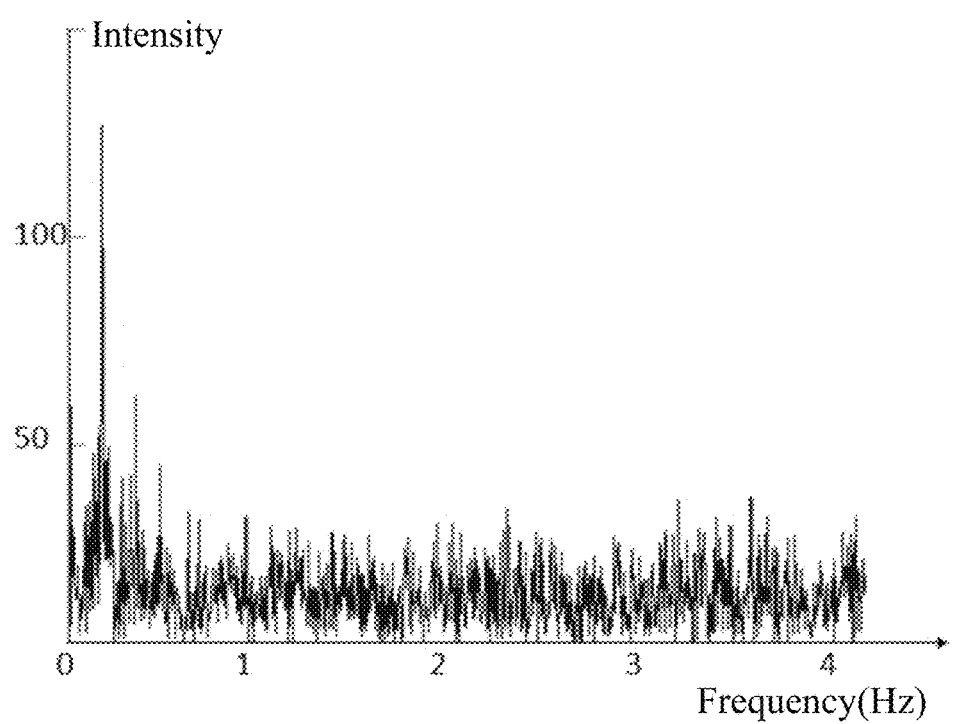
FIG. 16B illustrates the spectrum analysis of a weighted signal based on a characteristic VOI.
Figure 17:
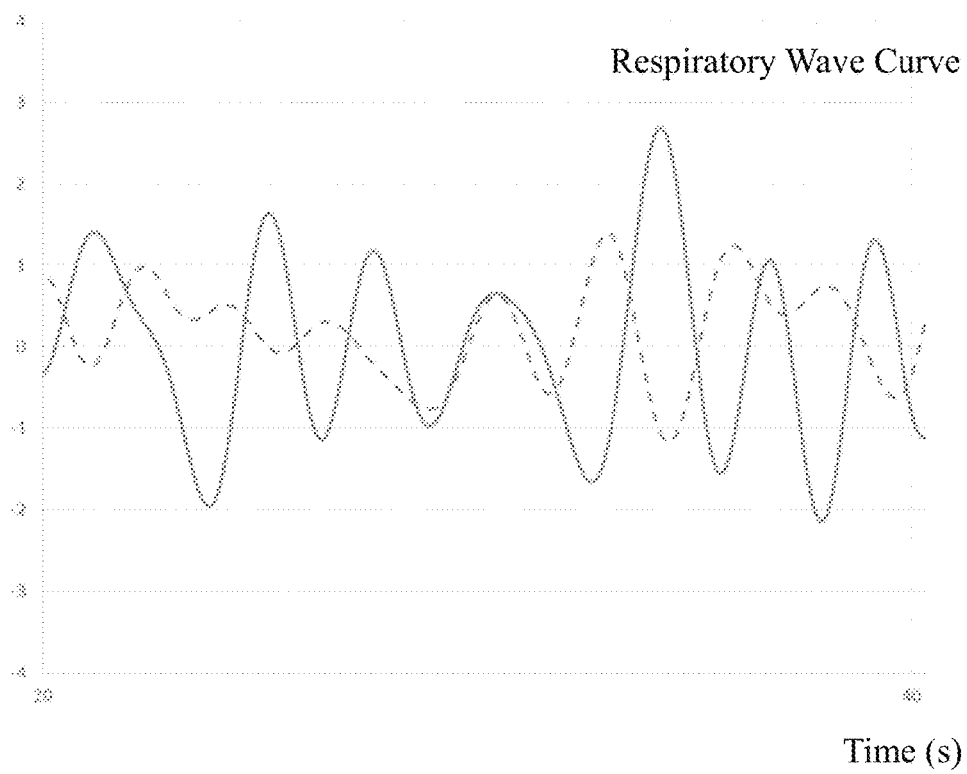
FIG. 17 illustrates a respiratory wave curve without reference to a characteristic VOI and a respiratory wave curve based on a characteristic VOI according to some embodiments of the present disclosure.

In step 803, a characteristic VOI may be determined based on the selected model. The characteristic VOI may be an optimal VOI according to some criteria based on the selected model. Merely by way of example, the value of SQI may be used as a criterion to optimize the choice of VOI. An exemplary process for obtaining a characteristic VOI may be found in FIG. 9 and the description thereof. In step 804, physiological motion information may be obtained based on a determined characteristic VOI. In some embodiments, the physiological motion information may include a physiological motion curve. An exemplary process for obtaining physiological motion information based on a characteristic VOI may be found in the FIG. 9 and the description thereof given below. A comparison may be seen between FIG. 16A and FIG. 16B, where FIG. 16A illustrates the spectrum analysis of a weighted signal without reference to a characteristic VOI, and FIG. 16B illustrates the spectrum analysis of a weighted signal based on a characteristic VOI. FIG. 17 illustrates a respiratory wave curve without reference to a characteristic VOI (solid line) and a respiratory wave curve based on a characteristic VOI (dotted line).

In step 805, raw ECT data may be gated based on the physiological motion information. In some embodiments, the raw ECT data may be gated based on the phase of the physiological motion curve. For example, the ECT data within the same phase of the physiological motion curve may be gated into the same subset. In some embodiments, the ECT data may be gated based on the amplitude of the physiological motion curve. One or more new images may then be reconstructed based on the gated ECT data in step 806.

Figure 9:
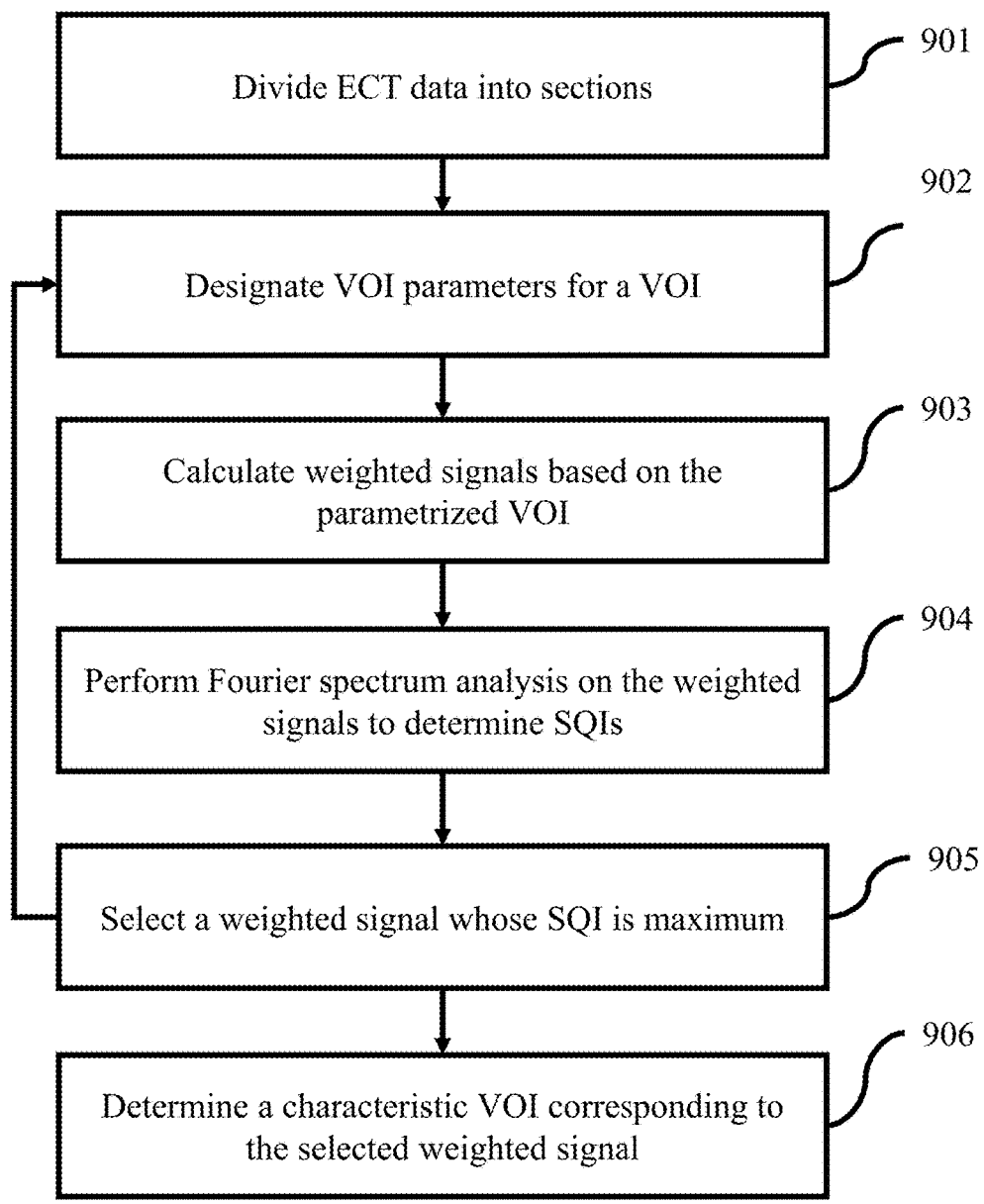
FIG. 9 is a flowchart illustrating an exemplary process for determining a characteristic VOI based on a set of ECT data according to some embodiments of the present disclosure.

FIG. 9 is a flowchart illustrating an exemplary process for determining a characteristic VOI based on a set of ECT data according to some embodiments of the present disclosure. Process 900 may be performed by processing logic including hardware (e.g., circuitry, dedicated logic, programmable logic, microcode, etc.), software (e.g., instructions run on a processing device to perform hardware simulation), or the like, or a combination thereof. In some implementations, process 900 may be performed by one or more processing devices (e.g., physiological motion detector 502 as described in FIG. 7) and elsewhere in the present disclosure.

In step 901, data such as ECT data may be divided into sections. The data may be divided into a plurality of sections that span, for example, approximately 100 milliseconds. Exemplary time span may be 5 seconds, 10 seconds, etc. In step 902, VOI parameters may be designated to identify the shape and/or the location of a VOI. As used herein, VOI parameters may include, for example, the parameters to identify the shape, volume, position of a VOI. Exemplary shapes of VOIs may be a sphere, a cuboid, a block, or the like, or any combination thereof. Exemplary parameters for identifying a sphere may be $(X_1, X_2, X_3)$ and $X_4$, namely the coordinates of the sphere center and the radius r of the sphere. Exemplary parameters for identifying a block may be $(X_1, X_2, X_3)$, $X_4$, $X_5$, and $X_6$, namely the coordinates of the center of the block, and the length, the width, and the height of the block. A shape of a complicated contour may be described using more parameters than a shape of a simple contour. In some embodiments, a shape that may be described using a set of VOI parameters including fewer than 10 parameters may be designated in step 902. In some embodiments, a shape that may be described using a set of VOI parameters including fewer than 20 parameters may be designated in step 902.

In step 903, a weighted signal may be calculated based on the data and the parametrized VOI. Merely by way of example, for the case of data being list mode ECT data, the coordinate representation of an annihilation event (or referred to as an event for brevity) $(s_e, \varphi, z_e, \theta, \lambda_e)$, or any other data that are familiar to a person of ordinary skills in the art, may be used. The specific meaning of the parameters $s_e, \varphi, z_e, \theta$ and $\lambda_e$ may be found in FIG. 12B where the $z_e$ may represent the intersection value of ▓▓▓▓ and the z axis, the z axis may be along the direction from the foot of a subject (e.g., a patient) to the head of the patient; $s_e$ and $\varphi$ may represent two coordinates of the list mode data, namely the radial distance and the angle of the projected line of response of ▓▓▓▓ ; $\theta$ is the angle of ▓▓▓▓ along the z direction; $\lambda_e$ may use Time-of-flight (TOF) method to record the distance between the event and the origin using, for example, a TOF based method, and the time information t.

The annihilation point (x, y, z) of an event may be calculated from the coordinate representation $(s_e, \varphi, z_e, \theta, \lambda_e)$ of the event as follows:

$$\begin{cases} x = s_e\cos(\varphi) - \lambda_e\cos(\theta)\sin(\varphi) \\ y = s_e\sin(\varphi) + \lambda_e\cos(\theta)\cos(\varphi) \\ \quad z = z_e + \lambda_e\sin(\theta) \end{cases} \quad \text{(Formula 2)}$$

In some embodiments, the accuracy of the parameter $\lambda_e$ may be improved, and an improved TOF coordinate of an event $\Lambda$ may be treated as a random variable of a probabilistic distribution as expressed in Formula 3:

$$P_e(\Lambda = \lambda) = \frac{1}{\sqrt{2\pi}\,\sigma} e^{-\frac{(\lambda_e - \lambda)^2}{2\sigma^2}}, \quad \text{(Formula 3)}$$

in which $\lambda_e$ is the expectation of the Gaussian distribution, $\sigma$ may be the variance of the Gaussian distribution which may be obtained based on the time resolution of the imaging system. Because the coordinate $\Lambda$ of a TOF may be treated as a random variable, the annihilation point of this event may also be a random variable depending upon $\Lambda$. The distribution probability of the annihilation point (x, y, z) may be expressed as $F_e(\vec{r} = (x, y, z)) = P_e(\Lambda = \lambda)$.

Accordingly, the probability distribution of an observed event at time t may be expressed as follows:

$$F(x,y,z,t) = \Sigma_{time(e)=t} F_e(\vec{r} = (x,y,z)). \quad \text{Formula 4}$$

After the probability distribution of an observed event at time t is obtained, a weighted signal indicating a physiological motion of a subject (e.g., the physiological motion of an inner organ of the subject), may be calculated as follows:

$$\text{Signal}(t) = \frac{\int_{FOV}\int_{\tau=t}^{\tau=t+\Delta T} F(x, y, z, t) w_1(x, y, z) dv d\tau}{\int_{FOV}\int_{\tau=t}^{\tau=t+\Delta T} F(x, y, z, t) w_2(x, y, z) dv d\tau}, \quad \text{Formula 5}$$

when $w_1(x, y, z) = z$, and $w_2(x, y, z) = 1$. A specific weighted signal indicating the movement of center of mass (COM) along z direction, may be obtained as follows:

$$COM(t) = \frac{\int_{FOV}\int_{\tau=t}^{\tau=t+\Delta T} F(x, y, z, t) z\, dv d\tau}{\int_{FOV}\int_{\tau=t}^{\tau=t+\Delta T} F(x, y, z, t) dv d\tau}. \quad \text{Formula 6}$$

In the Formulas 5 and 6, dv=dxdydz, that represents the differential of the volume, dτ is the differential of incident integral, integrated over the field of view (FOW). [t, t+ΔT] represents the time internal during which the event involved in F(x, y, z, t) occurs. ΔT is the time internal. In some embodiments, ΔT is 50 ms~1000 ms. The value of the time interval may be determined according to a sampling theorem. In some embodiments, the value of ΔT may be determined when there are a sufficient number of sample points. COM(t) may represent the distribution of the annihilations occurred along the z direction within an entire scan.

In some embodiments, a weighted signal based on a VOI, indicating the movement of the center of mass of the VOI, may be calculated as follows:

$$COM(t, V(x, y, z)) = \quad \text{Formula 7}$$
$$\frac{\int_{FOV}\int_{\tau=t}^{\tau=t+\Delta T} V(x, y, z) F(x, y, z, t) z\, dv d\tau}{\int_{FOV}\int_{\tau=t}^{\tau=t+\Delta T} V(x, y, z) F(x, y, z, t) dv d\tau}.$$

In Formula 7, V(x,y,z) may be an indicator function of a VOI, i.e. V(x, y, z) may take value 1 if (x, y, z) is located within the VOI, and zero if (x, y, z) is located outside of the VOI.

In step 904, a Fourier spectrum analysis may be performed on the weighted signals to determine signal quality indicator (SQI). As used herein, the signal quality indicator may refer to the signal-noise-ratio, which may compare the energy level of a target signal within a physiological spectrum, to the energy level of the target signal outside of the physiological spectrum. The energy level of a signal may be measured in terms of the spectral behavior of the signal.

Merely by way of example, as shown in the following Formula 8, a signal quality indicator (SQI) based on a physiological spectrum may be calculated as follows:

$$SNR(\text{signal}(t)) = \frac{\int_{f \in signal\_space} G_1(FT(\text{signal}(t))) df}{\int_{f \notin signal\_space} G_2(FT(\text{signal}(t))) df}, \quad \text{Formula 8}$$

where FT(signal(t)) is a Fourier transform of signal(t), f∈signal_space means that the frequency f falls within the physiological spectrum, and f∉signal_space indicates that the frequency f falls outside of the physiological spectrum. When a respiratory motion needs to be detected, the physiological spectrum for a respiratory signal may be chosen. When a cardiac motion needs to be detected, the physiological spectrum for a cardiac signal may be chosen. $G_1$ and $G_2$ are two functions measuring the energy level of the function g(f), where g(f) may be a function of f, $\|g(f)\|$ may be the absolute value of g(f). For example, $G_1$ and $G_2$ may be shown in Formula 9 as follows:

$$G_1(g(f)) = G_2(g(f)) = \|g(f)\|^2, \quad \text{Formula 9}$$

In step 905, SQI for a given VOI may be maximized by traversing the set of VOI parameters. Merely by way of example, a way of traversing the set of VOI parameters may be choosing a subset of VOI parameters and performing a traversing algorithm on the chosen subset of VOI parameters to accelerate the execution of the traversing algorithm.

In step 906, a characteristic VOI with the maximized SQI among the SQIs calculated in the step 905 may be determined. In some embodiments, a characteristic VOI may be determined by considering the behavior of SQI and other indicators jointly. For example, a characteristic VOI may be determined by maximizing a certain combination of SQI and the volume of a VOI.

Figure 10A:
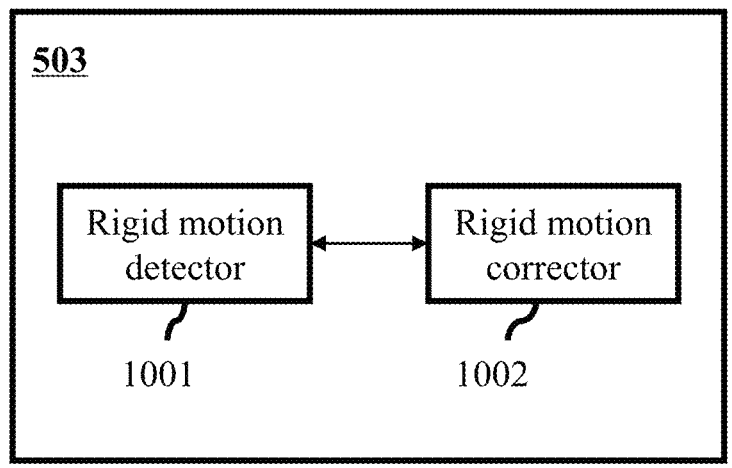
FIG. 10A is a block diagram illustrating an architecture of a rigid motion detector according to some embodiments of the present disclosure.

FIG. 10A is a block diagram illustrating an architecture of a rigid motion detector according to some embodiments of the present disclosure. The rigid motion processor 503 may include a rigid motion detector 1001 and a rigid motion corrector 1002. As illustrated in FIG. 10A, the rigid motion detector 1001 may analyze list mode data and determine rigid motion information including an occurrence of a rigid motion and/or amplitude of the rigid motion. As used herein, the list mode may refer to a data form used for storing the ECT data. In some embodiments, the occurrence of a rigid motion and/or the amplitude of the rigid motion may be determined according to a threshold method (see details in FIG. 11 and the description thereof). In some embodiments, the rigid motion detector 1001 may include a division unit (not shown in FIG. 10A). The division unit may be used to divide the ECT data into a plurality of subsets. The plurality of subsets may be processed analyzed, and motion information may be obtained.

The rigid motion corrector 1002 may correct the list mode data based on determined motion information. As described above, the occurrence of a rigid motion and/or the amplitude thereof may be determined. The rigid motion corrector 1002 may correct the list mode data in a specific subset in which motion information is determined. For example, the rigid motion corrector 1002 may remove the motion information from the subset based on a motion field matrix (see details in FIG. 13).

It should be noted that the above description is provided for the purposes of illustration, not intended to limit the scope of the present disclosure. For persons having ordinary skills in the art, multiple variations and modifications may be reduced to practice in the light of the present disclosure. However, those variations and modifications do not depart from the scope of the present disclosure.

Figure 10B:
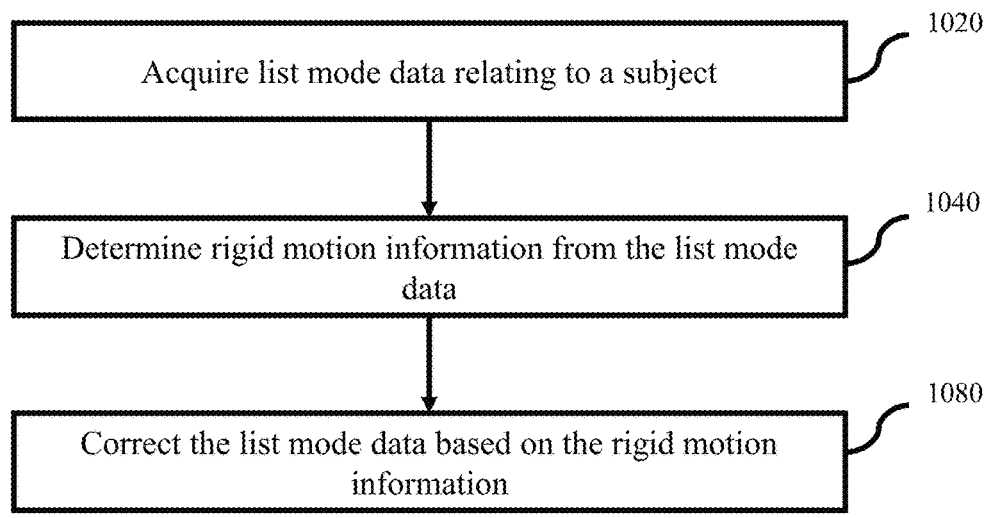
FIG. 10B a flowchart illustrating a process for rigid motion detection and correction according to some embodiments of the present disclosure.

FIG. 10B is a flowchart illustrating a process for rigid motion detection and correction according to some embodiments of the present disclosure. The process for rigid motion detection and correction may be performed by the rigid motion processor 503. The flowchart includes a process that may be carried out by one or more processors and/or electronic components under the control of computer-readable and/or computer-executable instructions. Although specific steps are disclosed in the flowcharts, such steps are exemplary. That is, the present embodiments are well suited to performing various other steps or variations of the steps recited in the flowchart. Within various embodiments, it should be appreciated that the steps of the flowchart may be performed by software, by hardware or by a combination of both.

As illustrated in FIG. 10B, in step 1020, the list mode data relating to a subject may be acquired. The list mode data may be acquired from the acquisition circuitry 202, the ECT data storage 201, or any storage disclosed anywhere in the present disclosure. In step 1040, rigid motion information may be detected or determined from the acquired list mode data. The detection may be based on measuring the similarity between the various subsets of list mode data directly, or based on measuring the similarity between the various images generated from the corresponding sets of list modes. The determination of rigid motion information may be based on the determination of a motion field matrix. In some embodiments, the information about a motion field matrix may be derived from a registration technique applied upon two different images. The technique of registration may include, but not limited to, LBFS method, Demons method. In some embodiments, the determination of rigid motion information may be based on the calculation of an expectation matrix. The detailed discussion about an expectation matrix may be found below.

In step 1080, the acquired list mode data may be corrected based on the rigid motion information. The correction may be performed on the list mode directly. In some embodiments, the correction may be performed on the images generated from the list mode data.

Figure 11:
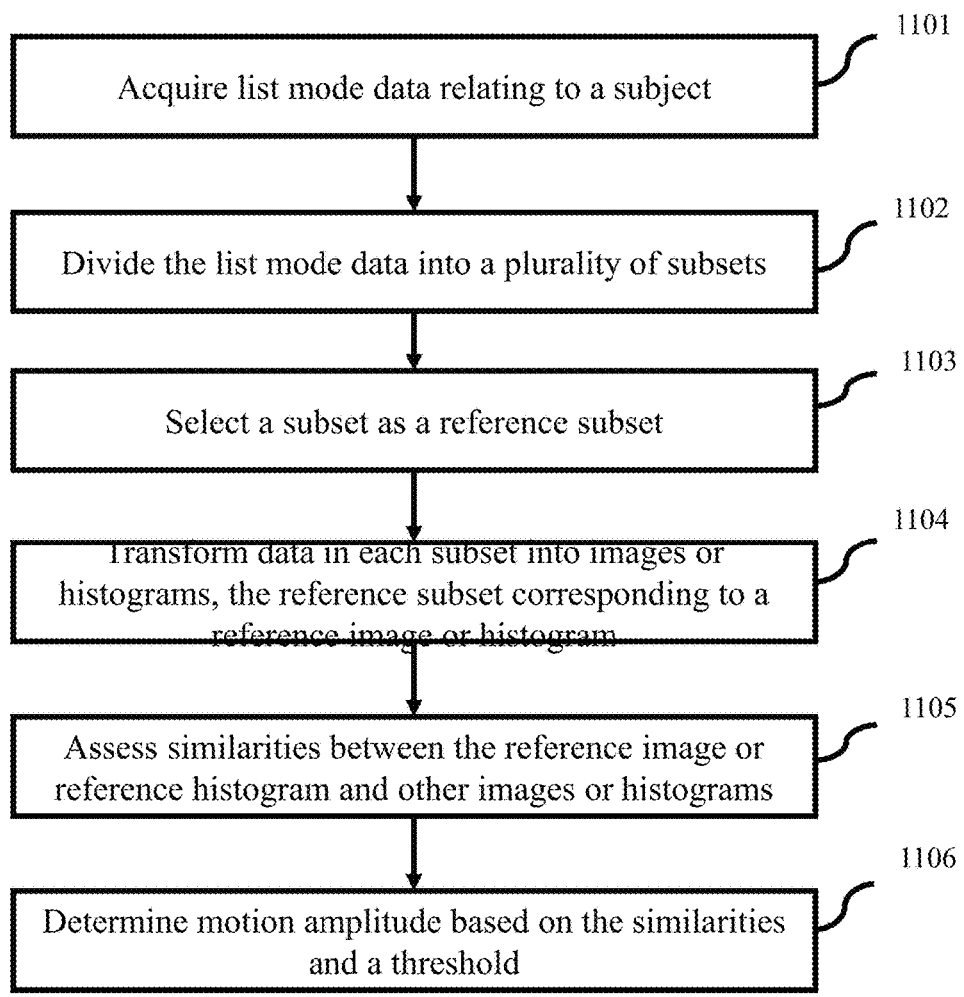
FIG. 11 is a flowchart illustrating a process for rigid motion detection according to some embodiments of the present disclosure.

FIG. 11 is a flowchart illustrating a process for rigid motion detection according to some embodiments of the present disclosure. The process for motion detection may be performed by the rigid motion detector 1001. The flowchart includes a process that may be carried out by one or more processors and/or electronic components under the control of computer-readable and/or computer-executable instructions. Although specific steps are disclosed in the flowcharts, such steps are exemplary. That is, the present embodiments are well suited to performing various other steps or variations of the steps recited in the flowchart. Within various embodiments, it should be appreciated that the steps of the flowchart may be performed by software, by hardware or by a combination of both.

As illustrated in FIG. 11, in step 1101, the list mode data related to a subject may be acquired. The list mode data may be acquired from the acquisition circuitry 202, the ECT data storage 201, or any storage disclosed anywhere in the present disclosure. In step 1102, the acquired list mode data may be divided into a plurality of subsets. The division may be performed by the division unit (not shown). In some embodiments, as is known, the list mode data may vary with respect to the acquisition time. The list mode data may be divided according to the acquisition time. For example, a specific subset may correspond to data acquired within a specific time interval. The time interval may be fixed or variable. For instance, the time interval may range from 1 second to 10 seconds. The time intervals of the plurality of subsets may be the same or different with each other. The divided plurality of subsets may be defined as:

$$S=\{s_i, 1 \leq i \leq T/\Delta t\},\qquad\text{Formula 10}$$

where $s_i$ may represent the $i^{th}$ subset divided from the list-mode data, T may represent the acquisition time of the list-mode data, and $\Delta t$ may represent the time interval.

In step 1103, one of the plurality of subsets may be selected as a reference subset. The selection may be performed based on a default setting of the imaging system 100 or an instruction from an operator (e.g., a doctor). In some embodiments, the first subset $S_1$ may be selected as the reference subset, and the reference subset may be expressed as $s_{ref}$.

In step 1104, the data in the plurality of subsets may be transformed into a plurality of images or histograms. In some embodiments, the data in the plurality of subsets may be transformed into a plurality of images according to the formula below:

$$img(x, y) = \sum_{ring_z} lor(crystal_x, crystal_y, ring_z),\qquad\text{Formula 11}$$

where $crystal_x$, $crystal_y$, $ring_z$ may represent identifiers of two scintillator crystals and scintillator ring corresponding to the LOR, respectively.

As mentioned above, the reference subset may correspond to a reference image. The reference image may be expressed as $img_{ref}$ while the other images transformed from the data in other subsets may be expressed as $img_i$.

In some embodiments, the data in the plurality of subsets may be transformed into a plurality of histograms. The reference subset may correspond to a reference histogram. The reference histogram may be expressed as $histo_{ref}$, while the other histograms transformed from the data in other subsets may be expressed as $histo_i$.

In step 1105, a similarity between the reference image or the reference histogram and other images or histograms may be assessed. In some embodiments, the similarity between the reference image and the other images may be obtained by:

$$I=\{I_i | I_i = \text{similarity}(img_{ref}, img_i), 1 \leq i \leq T/\Delta t\},\qquad\text{Formula 12}$$

where similarity(a, b) may represent the similarity function, $I_i$ may represent the similarity between the reference image ($img_{ref}$) and the $i^{th}$ image ($img_i$) corresponding to $i^{th}$ subset.

In some embodiments, the similarity between the reference histogram and the other histograms may be obtained by Formula 13 below. As used herein, the similarity may include shape similarity, distribution similarity, or the like, or a combination thereof.

$$I=\{I_i | I_i=\text{similarity}(histo_{ref}, histo_i), 1 \leq i \leq T/\Delta t\}, \quad \text{Formula 13}$$

where similarity(a, b) may represent the similarity function, and $I_i$ may represent the similarity between the reference histogram ($histo_{ref}$) and the $i^{th}$ histogram ($histo_i$) corresponding to $i^{th}$ subset.

In step 1106, an occurrence of a rigid motion and/or amplitude of the rigid motion may be determined based on the similarity and a threshold. The threshold may be set based on a default setting of the imaging system 100 or an instruction from an operator (e.g., a doctor). In some embodiment, the occurrence of the motion may be determined based on Formula 14 below.

$$I = \begin{cases} 0, & I_i \leq \text{threshold} \\ I_i, & I_i > \text{threshold} \end{cases}, \quad \text{Formula 14}$$

where 0 may mean that no motion have occurred, and $I_i$ may represent that a rigid motion has occurred within the time interval in which the $i^{th}$ subset is belong to.

Figure 12A:
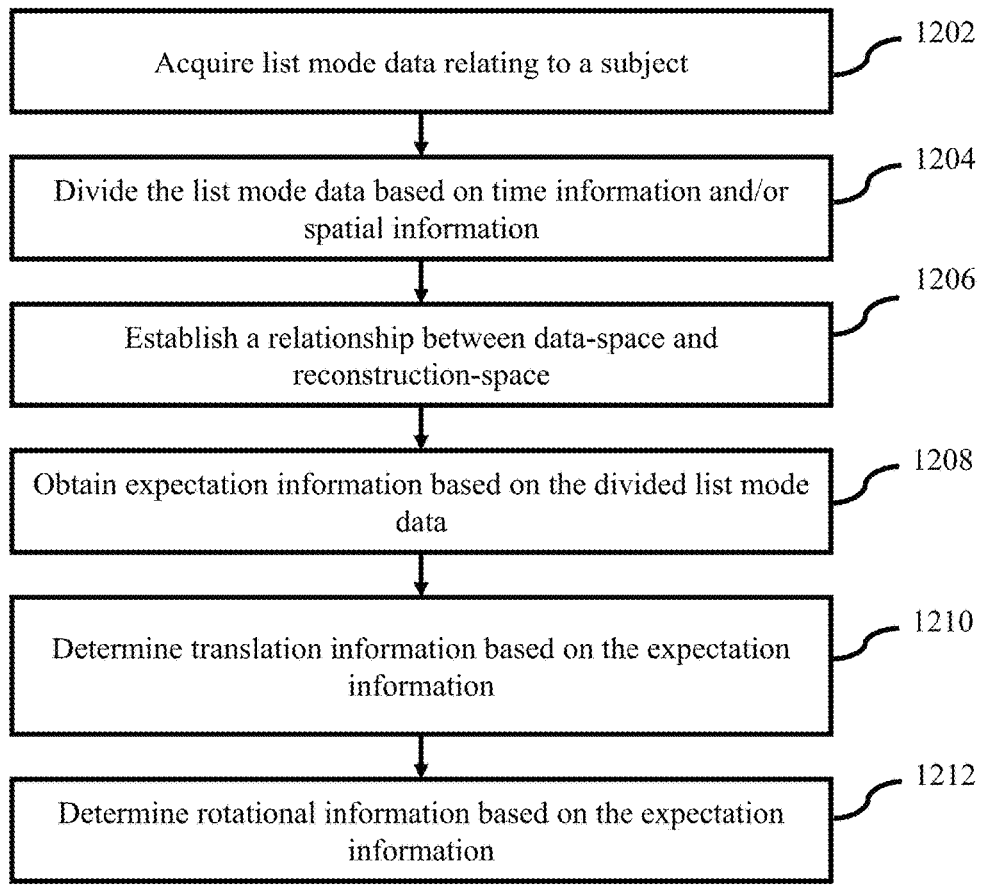
FIG. 12A is a flowchart illustrating a process for obtaining rigid motion information according to some embodiments of the present disclosure.

FIG. 12A is a flowchart illustrating a process for obtaining rigid motion information according to some embodiments of the present disclosure. The process for obtaining rigid motion information may be performed by the rigid motion processor 1001. The flowchart includes a process that may be carried out by one or more processors and/or electronic components under the control of computer-readable and/or computer-executable instructions. Although specific steps are disclosed in the flowcharts, such steps are exemplary. That is, the present embodiments are well suited to performing various other steps or variations of the steps recited in the flowchart. Within various embodiments, it should be appreciated that the steps of the flowchart may be performed by software, by hardware or by a combination of both.

In step 1202, list mode data relating to a subject may be acquired. The list mode data may be acquired from the acquisition circuitry 202, the ECT data storage 201, or any storage disclosed anywhere in the present disclosure.

In step 1204, the list mode data may be divided based on the time information and/or the spatial information. For example, the list mode data may be divided according to time span of 1 second or less. For another example, the list mode data may be divided according to time span of 5 seconds or less. As a further example, the list mode data may be divided according to time span of 10 seconds or less.

In step 1206, a relationship between the data space and the reconstruction space may be established. In some embodiments, data space may be given sinogram coordinates, and the reconstruction space may be given the 3D reconstruction coordinates. A relationship between sinogram coordinates and 3D reconstruction coordinates may be established (see details in FIG. 12B). The sinogram coordinates may include $\varphi$, s, z, and $\theta$. The 3D reconstruction coordinates may include the x-axis coordinate, the y-axis coordinate, and the z-axis coordinate. The relationship may be defined as:

$$s = x \cos(\varphi) + y \sin(\varphi), \quad \text{Formula 15}$$

where x may represent the x-axis coordinate, and y may represent the y-axis coordinate.

In step 1208, expectation information based on the divided list mode data may be obtained. Firstly, $P(\Phi, s, z, \theta, t)$ may represent the list mode data located at the sinogram coordinates ($\Phi$, s, z, $\theta$) at time t, by histogramming all events that are detected at time t. The list mode data $P(\Phi, s, z, \theta, t)$ may be divided into the time interval [$i\Delta T$, $(i+1)\Delta T$], $i=0, 1, \ldots$. At the n-th time interval [$n\Delta T$, $(n+1)\Delta T$], the rigid motion information may be obtained from the operation on the list mode data $P(\Phi, s, z, \theta, t)$, $t \in [n\Delta T, (n+1)\Delta T]$. Specifically, $E(S(\Phi, n))$ may represent the mathematical expectation of s with a projection angle $\Phi$ in the n-th time interval [$n\Delta T$, $(n+1)\Delta T$]. $E(S(\Phi, n))$ ($\Phi = \Phi_1, \Phi_2 \ldots \Phi_K$) may be calculated by:

$$E(S(\varphi, n)) = \frac{\int_{\tau=n\Delta T}^{\tau=(n+1)\Delta T} \left( \int_{All} s \cdot P(\varphi, s, z, \theta, \tau) ds d\theta dz \right) d\tau}{\int_{\tau=n\Delta T}^{\tau=(n+1)\Delta T} \left( \int_{All} P(\varphi, s, z, \theta, \tau) ds d\theta dz \right) d\tau}. \quad \text{Formula 16}$$

where $\varphi = \varphi_1, \varphi_2 \ldots \varphi_K$, and $\varphi_1, \varphi_2, \ldots, \varphi_K$ may represent candidate discrete values of $\varphi$.

In some embodiments, $E(S^2(\varphi, n))$ ($\varphi = \varphi_1, \varphi_2 \ldots \varphi_K$) may be calculated by $$E(S^2(\varphi, n)) = \\ \frac{\int_{\tau=n\Delta T}^{\tau=(n+1)\Delta T} \left( \int_{All} s^2 \cdot P(\varphi, s, z, \theta, \tau) ds d\theta dz \right) d\tau}{\int_{\tau=n\Delta T}^{\tau=(n+1)\Delta T} \left( \int_{All} P(\varphi, s, z, \theta, \tau) ds d\theta dz \right) d\tau} - E^2(S(\varphi, n)). \quad \text{Formula 17}$$

$E(X(n))$ and $E(Y(n))$ may represent mathematical expectations of translations of the subject's center of mass along the x axis and y axis, respectively in the $n^{th}$ time interval. $E(X(n))$ and $E(Y(n))$ may be calculated by:

$$\begin{pmatrix} \cos(\varphi_1) & \sin(\varphi_1) \\ \ldots & \ldots \\ \cos(\varphi_K) & \sin(\varphi_K) \end{pmatrix} \begin{pmatrix} E(X(n)) \\ E(Y(n)) \end{pmatrix} = \begin{pmatrix} E(S(\varphi_1, n)) \\ \ldots \\ E(S(\varphi_K, n)) \end{pmatrix}, \quad \text{Formula 18}$$

where $\varphi_1, \varphi_2, \ldots, \varphi_K$ may represent candidate discrete values of $\varphi$. In some embodiments, $K \geq 2$ may be sufficient to determine $E(X(n))$ and $E(Y(n))$, using, for example, the least square type methods. The distribution of $\varphi_1, \varphi_2, \ldots, \varphi_K$ may be uniform, i.e. the difference between $\varphi_i$ and $\varphi_{i-1}$, is invariant or independent of i. The distribution of $\varphi_1, \varphi_2, \ldots, \varphi_K$ may be non-uniform, i.e. the difference between $\varphi_i$ and $\varphi_{i-1}$ is not invariant or dependent of i.

In some embodiments, the translation of the subject's mass center along the z axis in the $n^{th}$ time interval may be defined as $E(Z(\theta, \varphi, n))$. $E(Z(\theta, \varphi, n))$ may be calculated by:

$$E(Z(\theta, \varphi, n)) = \frac{\int_{\tau=n\Delta T}^{\tau=(n+1)\Delta T} \left( \int_{All} z \cdot P(\varphi, s, z, \theta, \tau) ds dz \right) d\tau}{\int_{\tau=n\Delta T}^{\tau=(n+1)\Delta T} \left( \int_{All} P(\varphi, s, z, \theta, \tau) ds dz \right) d\tau}. \quad \text{Formula 19}$$

The covariance matrix $\mathcal{M}(n)$ may be calculated as $$\mathcal{M}(n) = \begin{pmatrix} E(X^2(n)) & E(X(n)Y(n)) & E(Z(n)X(n)) \\ E(X(n)Y(n)) & E(Y^2(n)) & E(Y(n)Z(n)) \\ E(Z(n)X(n)) & E(Y(n)Z(n)) & E(Z^2(n)) \end{pmatrix}$$ Formula 20 where $E(X^2(n))$, $E(Y^2(n))$, and $E(X(n)Y(n))$ may be calculated by $$\begin{pmatrix} \cos^2(\varphi_1) & \sin^2(\varphi_1) & 2\cos(\varphi_1)\sin(\varphi_1) \\ \cos^2(\varphi_2) & \sin^2(\varphi_2) & 2\cos(\varphi_2)\sin(\varphi_2) \\ \ldots & \ldots & \ldots \\ \cos^2(\varphi_K) & \sin^2(\varphi_K) & 2\cos(\varphi_K)\sin(\varphi_K) \end{pmatrix} \begin{pmatrix} E(X^2(n)) \\ E(Y^2(n)) \\ E(X(n)Y(n)) \end{pmatrix} =$$ Formula 21

$$\begin{pmatrix} E(S^2(\varphi_1, n)) \\ E(S^2(\varphi_2, n)) \\ \ldots \\ E(S^2(\varphi_K, n)) \end{pmatrix}.$$

In some embodiments, $K \geq 3$ may be sufficient to determine $E(X^2(n))$, $E(Y^2(n))$, and $E(X(n)Y(n))$ using, for example, the least square type methods. The distribution of $\varphi_1, \varphi_2, \ldots, \varphi_K$ may be uniform, i.e. the difference between $\varphi_i$ and $\varphi_{i-1}$ is invariant or independent of i. The distribution of $\varphi_1, \varphi_2, \ldots, \varphi_K$ may be non-uniform, i.e. the difference between $\varphi_i$ and $\varphi_{i-1}$ is not invariant or dependent of i.

$E(Z(n)X(n))$, and $E(Y(n)Z(n))$ may be calculated by $$\begin{pmatrix} \cos(\varphi_1) & \sin(\varphi_1) \\ \ldots & \ldots \\ \cos(\varphi_K) & \sin(\varphi_K) \end{pmatrix} \begin{pmatrix} E(Z(n)X(n)) + E(Z(n))E(X(n)) \\ E(Y(n)Z(n)) + E(Z(n))E(Y(n)) \end{pmatrix} =$$ Formula 22

$$\begin{pmatrix} E(Z(0, \varphi_1, n)S(0, \varphi_1, n)) \\ \ldots \\ E(Z(0, \varphi_K, n)S(0, \varphi_K, n)) \end{pmatrix}.$$

where $E(Z(\theta, \varphi, n)S(\theta, \varphi, n))$ ($\varphi = \varphi_1, \varphi_2 \ldots \varphi_K$) may be calculated by $$E(Z(\theta, \varphi, n)S(\theta, \varphi, n)) = \frac{\int_{\tau=n\Delta T}^{\tau=(n+1)\Delta T}\left(\int_{All} z \cdot s \cdot P(\varphi, s, z, \theta, \tau)dsdz\right)d\tau}{\int_{\tau=n\Delta T}^{\tau=(n+1)\Delta T}\left(\int_{All} P(\varphi, s, z, \theta, \tau)dsdz\right)d\tau}.$$ Formula 23

$E(Z^2(n))$ may be calculated by $$E(Z^2(n)) = E(Z^2(0,n)).$$ Formula 24 where $E(Z^2(0, n))$ may be calculated by $$E(Z^2(\theta, n)) = \frac{\int_{\tau=n\Delta T}^{\tau=(n+1)\Delta T}\left(\int_{All} z^2 \cdot P(\varphi, s, z, \theta, \tau)dsd\varphi dz\right)d\tau}{\int_{\tau=n\Delta T}^{\tau=(n+1)\Delta T}\left(\int_{All} P(\varphi, s, z, \theta, \tau)dsd\varphi dz\right)d\tau} -$$ Formula 25

$$\left(\int_{All} E(Z(\theta, \varphi, n))d\varphi\right)^2.$$

In step 1210, the translation information based on the expectation information may be obtained. As used herein, the term "translation information" may refer to a translational motion of a subject along the x axis, the y axis, and/or the z axis. For example, a translational motion of the subject's center of mass along the x axis, the y axis, and/or the z axis may be obtained and may be defined as U(n), V(n), and W(n), respectively.

U(n), V(n), and W(n) may be calculated by:

$$\begin{cases} U(n) = E(X(n)) - E(X(0)) \\ V(n) = E(Y(n)) - E(Y(0)) \\ W(n) = E(Z(n)) - E(Z(0)) = \int_{All} E(Z(0, \varphi, n)) - E(Z(0, \varphi, n))d\varphi \end{cases},$$ Formula 26 where $E(X(n))$ and $E(Y(n))$ may represent the mathematical expectation of translations of the subject's center of mass along the x axis and the y axis, respectively, in the $n^{th}$ time interval.

In step 1212, the rotation information based on the expectation information may be obtained. As used herein, the term "rotation information" may refer to the rotation angles of the subject around the x axis, the y axis, and/or the z axis. For example, rotation angles of the subject centered at the center of mass around the x axis, the y axis, and/or the z axis may be obtained and may be defined as $\alpha(n)$, $\beta(n)$, and $\gamma(n)$, respectively. The angles $\alpha(n)$, $\beta(n)$, and $\gamma(n)$ may be calculated by:

$$\begin{cases} \alpha(n) = \arcsin(-r_{32}(n)/\cos(\beta(n))) \\ \beta(n) = \arcsin(r_{31}(n)) \\ \gamma(n) = \arcsin(-r_{21}(n)/\cos(\beta(n))) \end{cases}.$$ Formula 27 where $r_{32}(n)$, $r_{31}(n)$, and $r_{21}(n)$ may be calculated by $$R(n) = \mathcal{H}(n)\mathcal{H}^{-1}(0) = \begin{pmatrix} r_{11}(n) & r_{12}(n) & r_{13}(n) \\ r_{21}(n) & r_{22}(n) & r_{23}(n) \\ r_{31}(n) & r_{32}(n) & r_{33}(n) \end{pmatrix}$$ Formula 28 where R(n) may represent the rotation matrix of the patient, and R(n) may be $R_x*R_y*R_z$ as given in Formula 1, and $\mathcal{H}(n)$ may represent the eigen-vector matrix for the covariance matrix $\mathcal{M}(n)$. $\mathcal{H}(n)$ may be calculated by $$\mathcal{M}(n)\mathcal{H}(n) = \mathcal{H}(n)\lambda(n)$$ Formula 29 where $\lambda(n)$ may represent a 3×3 diagonal matrix, and $\mathcal{M}(n)$ may represent the covariance matrix given above.

The translation information (such as the translational motion of the subject's center of mass along the x axis, the y axis, and/or the z axis, denoted as U(n), V(n), and W(n), n=0, 1, 2, . . . respectively) may be used together with the rotational information (such as the angles $\alpha(n)$, $\beta(n)$, and $\gamma(n)$, n=0, 1, 2, . . . ) to detect the rigid motion of the subject. The detection may be based on a threshold. For example, if the magnitude of translation information (U(n), V(n), W(n)) is larger than or equal to a threshold, then the subject may be deemed to be undergoing rigid motion movement during the n-th time interval. For another example, if the magnitude of angles ($\alpha(n)$, $\beta(n)$, $\gamma(n)$) is larger than or equal to a threshold, then the subject may be deemed to be undergoing rigid motion movement during the n-th time interval. For a further example, if the magnitude of translation/rotational information (U(n), V(n), W(n), α(n), β(n), γ(n)) is larger than or equal to a threshold, then the subject may be deemed to be undergoing rigid motion movement during the n-th time interval. The magnitude of a quantity $(C_1, C_2, \ldots, C_k)$ may be calculated by $\sqrt{C1^2+C2^2+\ldots+Ck^2}$.

Besides the detection of rigid motion of the subject, the translation information (such as the translational motion of the subject's center of mass along the x axis, the y axis, and/or the z axis, denoted as U(n), V(n), and W(n), respectively) may be used together with the rotational information (such as the angles α(n), β(n), and γ(n)) to gate or subgate the list mode data. The gating may be performed in either an automatic or a manual way. For example, the list mode data in the n-th time interval may be subgated so that neither the magnitude of translation information nor the magnitude of rotational information of the subject within the subgated time intervals exceeds a predetermined threshold.

It should be noted that the above description is provided for the purposes of illustration, not intended to limit the scope of the present disclosure. For persons having ordinary skills in the art, multiple variations and modifications may be reduced to practice in the light of the present disclosure. However, those variations and modifications do not depart from the scope of the present disclosure. For example, to detect the rigid motion of the subject, a person of ordinary skill in the art may consider using the difference of translation information between two consecutive time intervals to detect the rigid motion. If the difference of translation information (or rotational information, or the like, or a combination thereof) between two consecutive time intervals is larger than or equal to a threshold, then the subject may be deemed to be undergoing rigid motion movement during the transition of the two consecutive time intervals. For a further example, if the difference between the covariance matrices for two consecutive time intervals is larger than or equal to a threshold, then the subject may be deemed to be undergoing rigid motion movement during the transition of the two consecutive time intervals.

Furthermore, the translation information (such as the translational motion of the subject's center of mass along the x axis, the y axis, and/or the z axis, denoted as U(n), V(n), and W(n), respectively may be used together with the rotational information (such as the angles α(n), β(n), and γ(n)) to correct the artifact caused by the rigid motion of the subject in the list mode data, the sinograms, or the reconstructed images. The artifact correction may be performed in either an automatic or a manual way. The artifact correction may be performed in an "in situ" way. For example, the reconstructed images may undergo a transformation of translation and/or rotation to counter the translation and/or rotation induced by U(n), V(n), and W(n) and the rotation angles α(n), β(n), and γ(n).

Figure 12B:
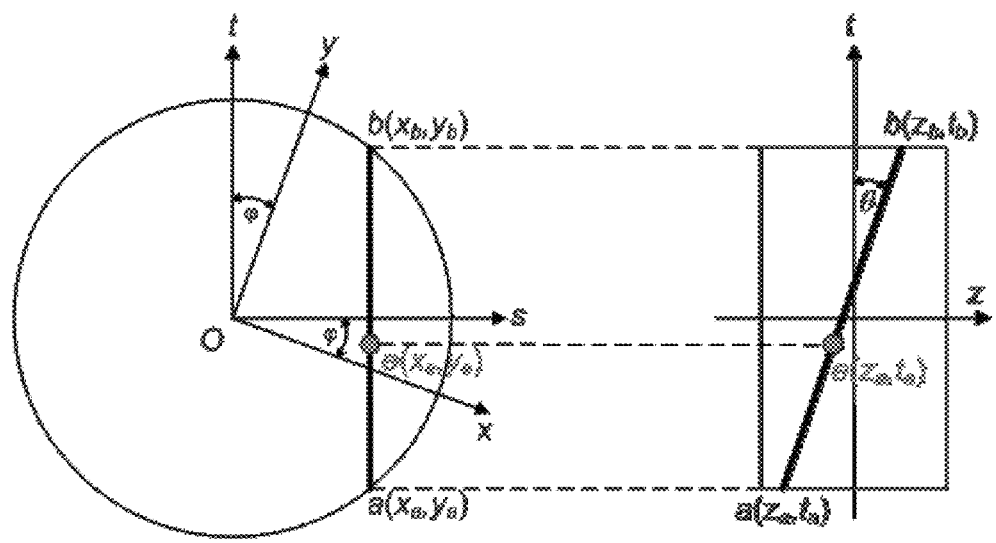
FIG. 12B illustrates a functional relationship between sinogram coordinates and 3D reconstruction coordinates according to some embodiments of the present disclosure.

FIG. 12B illustrates a functional relationship between sinogram coordinates and 3D reconstruction coordinates according to some embodiments of the present disclosure. As illustrated in FIG. 12B, Φ may represent the projection angle, s may represent the projection position, z may represent the axial position, θ may represent the angle with axial plane, and t may represent the time. The two points $a(x_a, y_a)$ and $b(x_b, y_b)$ give the two endpoints of the projected line of response, respectively. In FIG. 12B, the sinogrm coordinates are illustrated in the left part, and the 3D reconstruction coordinates are illustrated in the right part, where a and b are the indices of the detector pair, e represents an event, $x_e$ represents the x coordinate for the event e, t represents TOF coordinate, and z represents the axial position.

FIG. 13 is a flowchart illustrating a process for rigid motion correction according to some embodiments of the present disclosure. The process for motion correction may be performed by the rigid motion corrector 1002. The motion correction may be performed based on the motion information determined by the process 1100. The flowchart includes a process that may be carried out by one or more processors and/or electronic components under the control of computer-readable and/or computer-executable instructions. Although specific steps are disclosed in the flowcharts, such steps are exemplary. That is, the present embodiments are well suited to performing various other steps or variations of the steps recited in the flowchart. Within various embodiments, it should be appreciated that the steps of the flowchart may be performed by software, by hardware or by a combination of both.

In step 1301, the information, such as the amplitude of the motion, may be loaded. As illustrated in FIG. 11, the amplitude of the rigid motion may be determined based on the similarity and the threshold. In step 1302, the ECT data, such as the list mode data, may be gated based on the information, such as the amplitude of the motion. In some embodiments, gradient of the motion between I(i) and I(i−1) for i=1, 2, . . . , N may be calculated based on the similarity by the formula below.

$$\nabla I = I(i) - I(i-1) \qquad \text{Formula 30}$$

where I(i) may represent the similarity corresponding to the $i^{th}$ time interval.

The list mode data may be gated based on the gradient values and a threshold and a plurality of gates (also referred to as "gated list mode data sets") may be generated. The threshold may be set based on a default setting of the imaging system 100 or an instruction from an operator (e.g., a doctor). In some embodiments, data in the $i^{th}$ subset may be combined with that in the $(i-1)^{th}$ subset if the gradient between the $i^{th}$ time interval and $(i-1)^{th}$ time interval does not exceed a threshold. Otherwise, data in the $i^{th}$ subset may be classified into a new data set. The plurality of gated list mode data sets may be defined as:

$$D = \{D_i, 1 \leq i \leq n\} \qquad \text{Formula 31}$$

where n may represent the number of gated list-mode data set, and $D_i$ may represent the $i^{th}$ gated List-mode data set.

In step 1303, an image reconstruction may be performed based on gated list-mode data. The image reconstruction may be performed by the image reconstruction processor 207. The reconstructed images may be defined as:

$$f = \{f(D_i), 1 \leq i \leq n\} \qquad \text{Formula 32}$$

where $f(D_i)$ may represent the reconstructed image corresponding to the $i^{th}$ gated list-mode data set.

In step 1304, a reconstructed image may be selected as a reference image. The selection may be performed based on a default setting of the imaging system 100 or an instruction from an operator (e.g., a doctor). In some embodiments, the image corresponding to the first gated list-mode data set may be selected as the reference image.

In step 1305, an image registration may be performed to obtain a motion field matrix. The image registration may be performed between the reference image and other reconstructed images. Methods used for the image registration may include a cross-correlation (CC), a normalized CC, a sequential similarity detection algorithm (SSDA), a mutual information (MI) method, a sum of squared intensity differences, a ratio image uniformity, or the like, or a combination thereof. In some embodiments, the motion field matrix may be defined as:

$$T=\{T_i, 1 \leq i \leq n\} \quad \text{Formula 33}$$

The motion field matrix may be calculated by Formula 1 as already described.

In step 1306, the list mode data may be corrected based on the motion field matrix. In some embodiments, the imaging system 100 may correct the spatial information of the list mode data based on the motion field matrix. As used herein, the term "spatial information" may refer to spatial coordinates of a pair of scintillator crystals in a PET system corresponding to an LOR. Exemplary spatial information may be defined as:

$$(\vec{x}_a, \vec{x}_b) = \begin{cases} \vec{x}_a = (x_a, y_a, z_a) \\ \vec{x}_b = (x_b, y_b, z_b) \end{cases} \quad \text{Formula 34}$$

where $$\vec{x}_a$$

may represent the space coordinates of $crystal_a$;

$$\vec{x}_b$$

may represent the space coordinates of $crystal_b$; $x_a$, $y_a$ and $z_a$ may represent the x-axis coordinate, y-axis coordinate, and z-axis coordinate of $crystal_a$ respectively; $x_b$, $y_b$ and $z_b$ may represent the x-axis coordinate, the y-axis coordinate, and/or the z-axis coordinate of $crystal_b$, respectively.

The space coordinates of a pair of scintillator crystals may be corrected by the following formula:

$$\begin{bmatrix} \vec{x}_a' \\ \vec{x}_b' \end{bmatrix} = \begin{bmatrix} T & o \\ o & T \end{bmatrix} \begin{bmatrix} \vec{x}_a \\ \vec{x}_b \end{bmatrix} \quad \text{Formula 35}$$

where $$\vec{x}_a'$$

may represent the corrected space coordinates of $crystal_a$, and $$\vec{x}_b'$$

may represent the corrected space coordinates of $crystal_b$.

In some embodiments, the imaging system 100 may correct spatial information and time information of the list mode data based on the motion field matrix. In some embodiments, the format of the list mode data may be defined as:

$$(\vec{x}_a, \vec{x}_b, t) = \begin{cases} \vec{x}_a = (x_a, y_a, z_a) \\ \vec{x}_b = (x_b, y_b, z_b) \\ t = (t_a, t_b) \end{cases} \quad \text{Formula 36}$$

where $t_a$ and $t_b$ represent time of flight (TOF) corresponding to $crystal_a$ and $crystal_b$, respectively.

With a high timing resolution, the space coordinates of event may be localized based on the list mode data. Taking into consideration the timing resolution of the imaging system 100 a maximum likelihood point (MLP) may be obtained together with the probability distribution centered with MLP along the LOR. The MLP may be calculated by the following formula:

$$\vec{x}_0^r = 1/2 * c * (t_b - t_a) * \left( (\vec{x}_b^r - \vec{x}_a^r) / |\vec{x}_b^r - \vec{x}_a^r| \right) + (\vec{x}_b^r + \vec{x}_a^r)/2 \quad \text{Formula 37}$$

where c may represent speed of light.

According to Formula 37, the format of the list mode data may be defined as:

$$(\vec{x}_a^r, \vec{x}_b^r, \vec{x}_0^r) = \quad \text{Formula 38}$$

$$\begin{cases} \vec{x}_a^r = (x_a, y_a, z_a) \\ \vec{x}_b^r = (x_b, y_b, z_b) \\ 1/2 * c * (t_b - t_a) * ((\vec{x}_b^r - \vec{x}_a^r)/|\vec{x}_b^r - \vec{x}_a^r|) + (\vec{x}_b^r + \vec{x}_a^r)/2 \end{cases}$$

The probability distribution centered with MLP along the LOR may be symmetrical. A new probability distribution may be obtained with a corrected space coordinates of MLP. The list mode data may be corrected with the following formula:

$$\begin{bmatrix} \vec{x}_a' \\ \vec{x}_b' \\ \vec{x}_0' \end{bmatrix} = \begin{bmatrix} T & o & o \\ o & T & o \\ o & o & T \end{bmatrix} \begin{bmatrix} \vec{x}_b \\ \vec{x}_b \\ \vec{x}_0 \end{bmatrix} \quad \text{Formula 39}$$

where $$\vec{x}_0'$$

may represent the corrected space coordinates of MLP.

In an optional step 1307, an image reconstruction may be performed based on the corrected list mode data. The image reconstruction may be performed by the mage reconstruction processor 207.

It should be noted that the above embodiments are provided for the purposes of illustration, and not intended to limit the scope of the present disclosure. After consulting the present disclosure, one skilled in the art may envisage numerous other changes, substitutions, variations, alterations, and modifications without inventive activity, and it is intended that the present disclosure encompasses all such changes, substitutions, variations, alterations, and modifications, as falling within its scope.

EXAMPLES

The following examples are provided for illustration purposes, and not intended to limit the scope of the present disclosure.

Example 1

Figure 14:
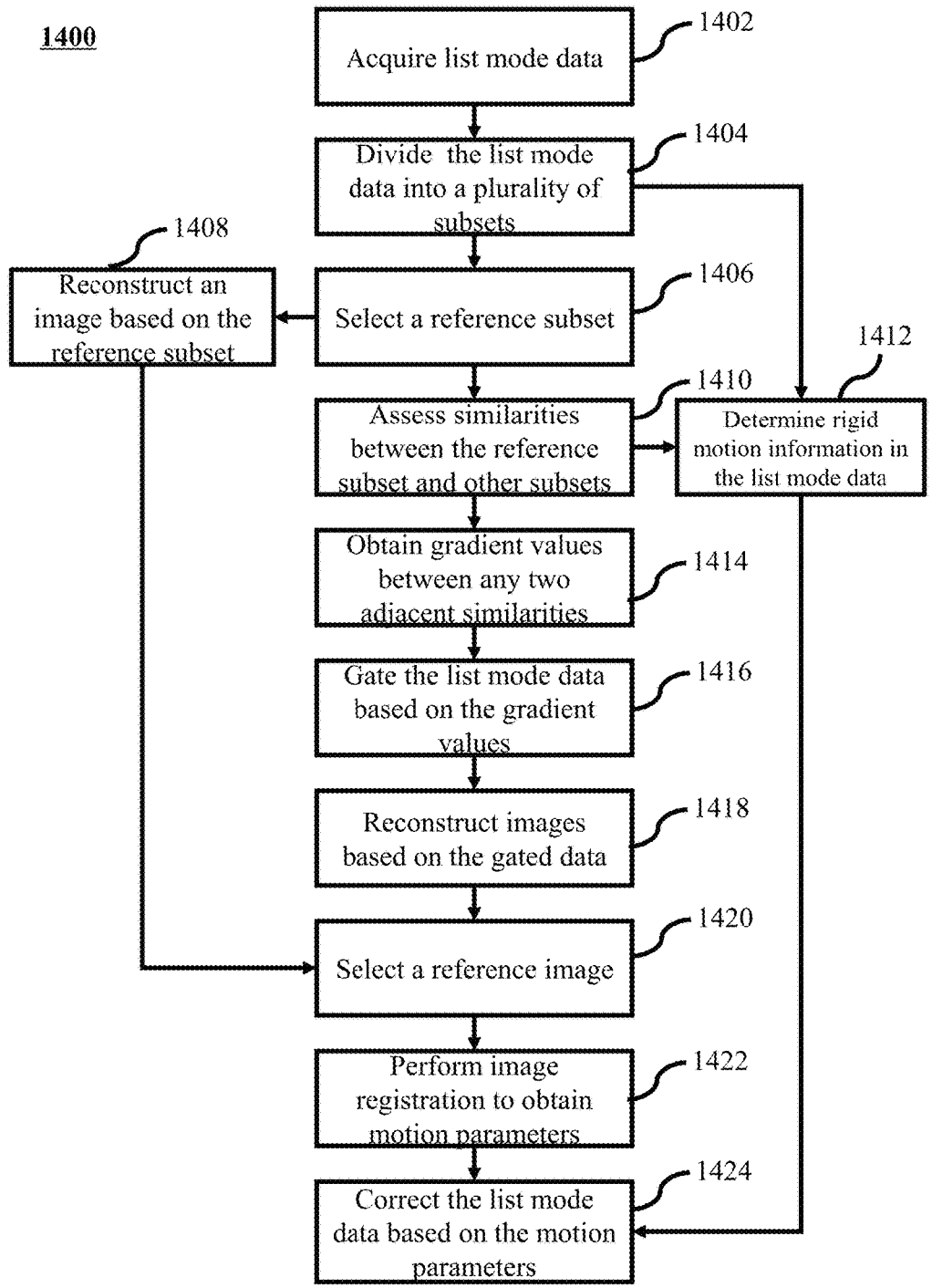
FIG. 14 provides an exemplary process for motion correction according to some embodiments of the present disclosure.

FIG. 14 provides an exemplary process for motion correction according to some embodiments of the present disclosure. The process 1400 may be performed by the rigid motion processor 503. The flowchart includes a process that may be carried out by one or more processors and/or electronic components under the control of computer-readable and/or computer-executable instructions. Although specific steps are disclosed in the flowcharts, such steps are exemplary. That is, the present embodiments are well suited to performing various other steps or variations of the steps recited in the flowchart. Within various embodiments, it should be appreciated that the steps of the flowchart may be performed by software, by hardware or by a combination of both.

In step 1402, list mode data may be acquired. The list mode data may be acquired the acquisition circuitry 202, the ECT data storage 201, or any storage disclosed anywhere in the present disclosure. In step 1404, the list mode data may be divided into a plurality of subsets according to a fixed acquisition time interval. The time interval may range from 1 second to 10 seconds. In step 1406, one of the plurality of subsets may be selected as a reference subset. In some embodiments, the subset $S_1$ corresponding to the first time interval may be selected as the reference subset. In some embodiments, multi-frame subsets may be obtained. As used herein, the multi-frame subset may refer to the subsets other than the reference subset. In some embodiments, the reference subset and the multi-frame subsets may be obtained simultaneously or successively.

In step 1408, an image may be reconstructed based on the reference subset. The reconstructed image may be designated as reference image for further usage in step 1420 to be described later.

In step 1410, similarities between the reference subset and the other subsets may be assessed respectively (detailed descriptions regarding the similarity may be found in FIG. 11). Based on the similarity information derived from step 1410, rigid motion information may be obtained in the list mode data in step 1412 (detailed descriptions regarding obtaining rigid motion information may be found in FIG. 11). In step 1414, gradient between any two similarities may be obtained. In step 1416, the list mode data may be gated based on the gradient values. In step 1418, images may be reconstructed based on the gated list mode data. In step 1420, a reference image may be selected from the reconstructed images. The reference image and the other images may be obtained simultaneously or successively. In step 1422, an image registration may be performed between the reference image and other reconstructed images. Methods for image registration may include a cross-correlation (CC), a normalized CC, a sequential similarity detection algorithm (SSDA), a mutual information (MI) method, a sum of squared intensity differences, a ratio image uniformity, or the like, or a combination thereof. As a consequence of image registration between the reference image and other reconstructed images, motion parameters may be obtained. The motion parameters may include rotation matrix around the x-axis, rotation matrix around the y-axis, rotation matrix around the z-axis, the translation matrix, the motion field matrix, or the like. In step 1424, the list mode data may be corrected based on the motion parameters. In some embodiments, spatial information and/or time information of the list mode data may be corrected.

Example 2

FIG. 18A through FIG. 18D provide four exemplary gated images with and/or without the process of correction. FIG. 18A and FIG. 18B give two exemplary gated images without the process of correction illustrated in the present disclosure, whereas FIG. 18C and FIG. 18D give two exemplary gated images according to the process of correction illustrated in FIG. 11 of the present disclosure. It may be seen from the comparison of FIG. 18A and FIG. 18C that the corrected gated image in FIG. 18C exhibits less artifacts than the gated image in FIG. 18A. Similar effect of artifact reducing may be seen from the comparison of FIG. 18B and FIG. 18D.

Example 3

Figure 19A:
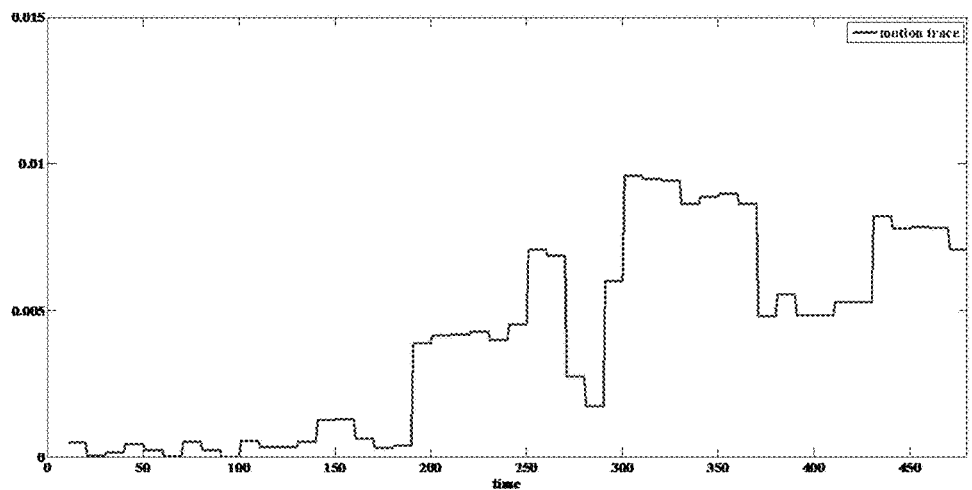
FIG. 19A provides one exemplary motion curve according to some embodiments of the present disclosure.
Figure 19B:
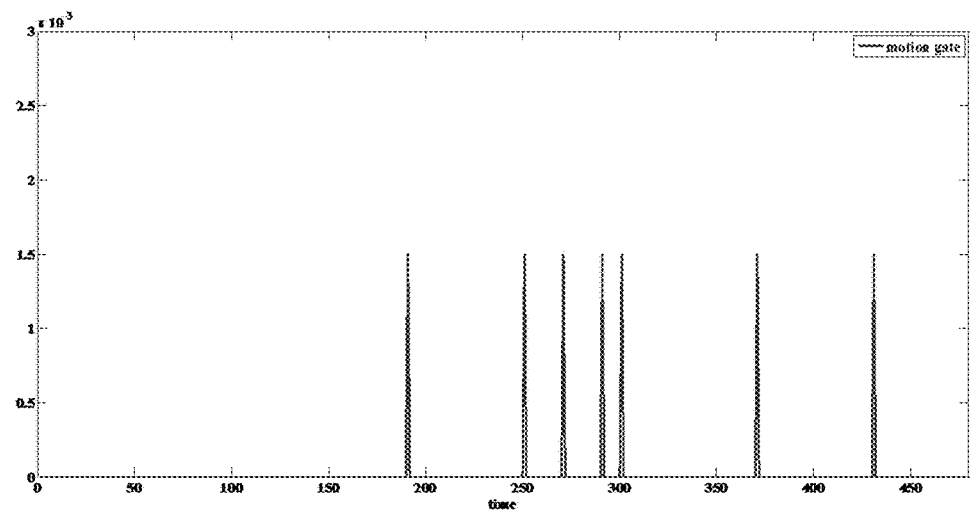
FIG. 19B provides one exemplary curve illustrating motion gates according to some embodiments of the present disclosure.

FIG. 19A provides one exemplary motion curve according to some embodiments of the present disclosure. As illustrated in FIG. 19A, the motion amplitude, whose values represent the similarities between the reference subset and the other subsets, varied with respect to time. The motion gates at various times were illustrated in FIG. 19B. The list mode data was gated and the rigid motion was extracted according to the motion gates as shown in FIG. 19B.

Figure 20A:
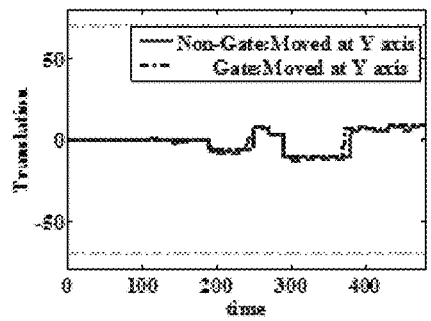
FIG. 20A provides two exemplary motion curves according to some embodiments of the present disclosure.
Figure 20B:
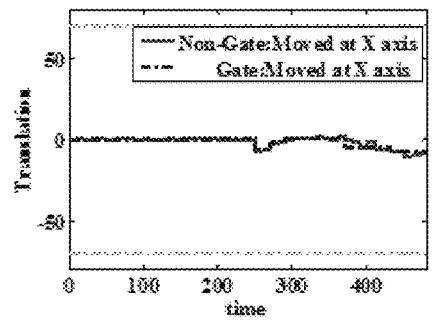
FIG. 20B provides two exemplary motion curves according to some embodiments of the present disclosure.
Figure 20C:
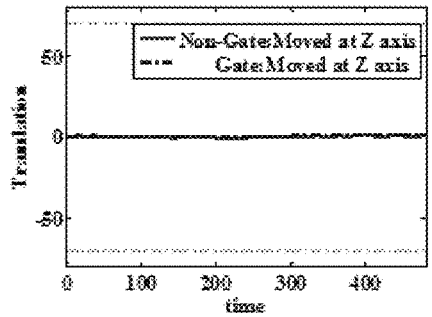
FIG. 20C provides two exemplary motion curves according to some embodiments of the present disclosure.
Figure 20D:
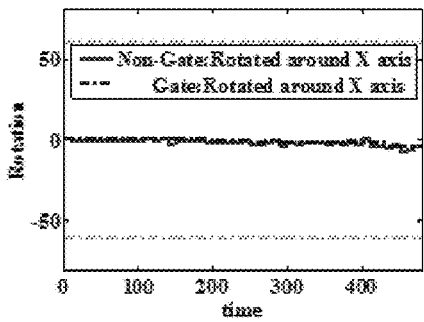
FIG. 20D provides two exemplary motion curves according to some embodiments of the present disclosure.
Figure 20E:
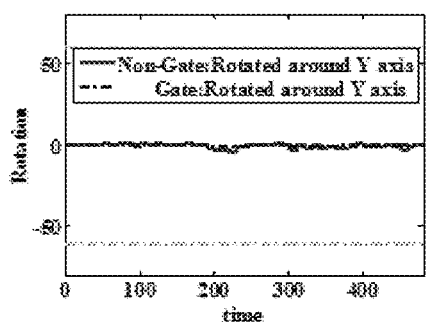
FIG. 20E provides two exemplary motion curves according to some embodiments of the present disclosure.
Figure 20F:
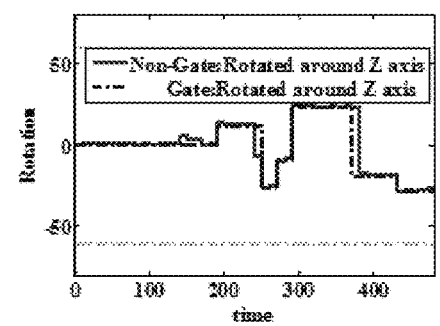
FIG. 20F provides two exemplary motion curves according to some embodiments of the present disclosure. One motion curve described rotation around the Z axis for the non-gated list mode data, whereas the other motion curve described rotation around the Z axis for the gated list mode data.

Processes of reconstructing images based on the gated data, selecting a reference image, and then performing image registration to obtain motion parameters were shown in FIG. 20A through FIG. 20F. FIG. 20A provides two exemplary motion curves according to some embodiments of the present disclosure. One motion curve described movement along the Y axis for the non-gated list mode data, whereas the other motion curve described movement along the Y axis for the gated list mode data. FIG. 20B provides two exemplary motion curves according to some embodiments of the present disclosure. One motion curve described movement along the X axis for the non-gated list mode data, whereas the other motion curve described movement along the X axis for the gated list mode data. FIG. 20C provides two exemplary motion curves according to some embodiments of the present disclosure. One motion curve described movement along the Z axis for the non-gated list mode data, whereas the other motion curve described movement along the Z axis for the gated list mode data. FIG. 20D provides two exemplary motion curves according to some embodiments of the present disclosure. One motion curve described rotation around the X axis for the non-gated list mode data, whereas the other motion curve described rotation around the X axis for the gated list mode data. FIG. 20E provides two exemplary motion curves according to some embodiments of the present disclosure. One motion curve described rotation around the Y axis for the non-gated list mode data, whereas the other motion curve described rotation around the Y axis for the gated list mode data. FIG. 20F provides two exemplary motion curves according to some embodiments of the present disclosure. One motion curve described rotation around the Z axis for the non-gated list mode data, whereas the other motion curve described rotation around the Z axis for the gated list mode data. From FIG. 20A-20F, it may been seen an agreement of the motion curves generated according to the present disclosure with the original motion curves.

Example 4

Figure 21:
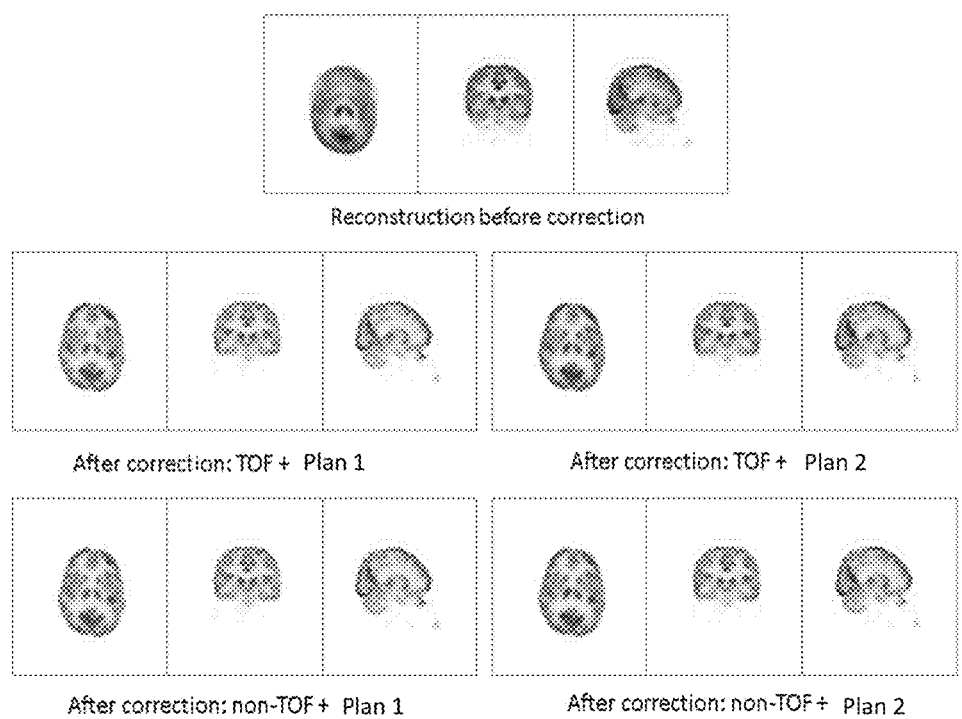
FIG. 21 provides several images reconstructed based on ECT data acquired from the brain according to some embodiments of the present disclosure.

FIG. 21 provides several images reconstructed based on ECT data acquired from the brain according to some embodiments of the present disclosure. As shown in FIG. 21, the list mode data was corrected based on the motion parameters. In the upper part of FIG. 21, it was shown three reconstructed brain images without correction. In the middle part, it was shown two groups of reconstructed images (with TOF) after correction. The left of middle part were corrected images according to original motion parameters, whereas the right of middle part were corrected images based on motion parameters generated according to the present disclosure. In the lower part, it was shown two groups of images (without TOF) after correction, in which the left of low part were corrected images according to original motion parameters, whereas the right of low part were corrected images based on motion parameters generated according to the present disclosure.

Example 5

Figure 22:
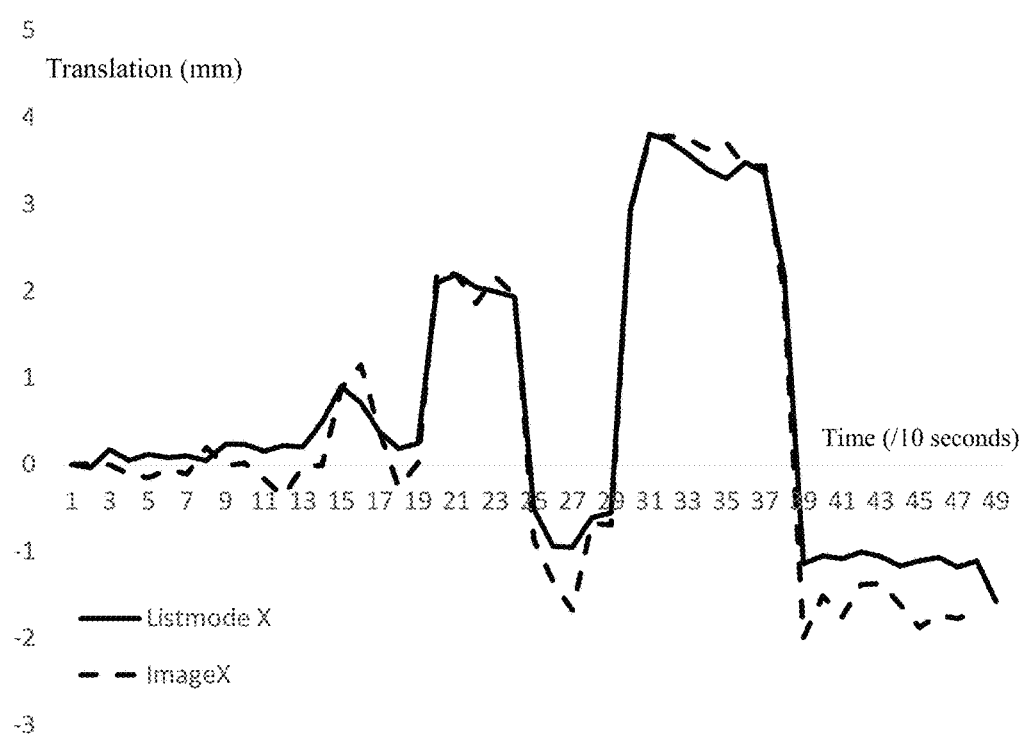
FIG. 22 provides a comparison between translations along the x-axis obtained based on different methods according to some embodiments of the present disclosure.

FIG. 22 provides a comparison between translations along the x-axis obtained based on different methods according to some embodiments of the present disclosure. As illustrated, the solid line may represent the translation of the subject along the x-axis obtained by the method disclosed in the present disclosure. The dotted line may represent the translation of the subject along the x-axis obtained based on image registration after image reconstruction.

Example 6

Figure 23:
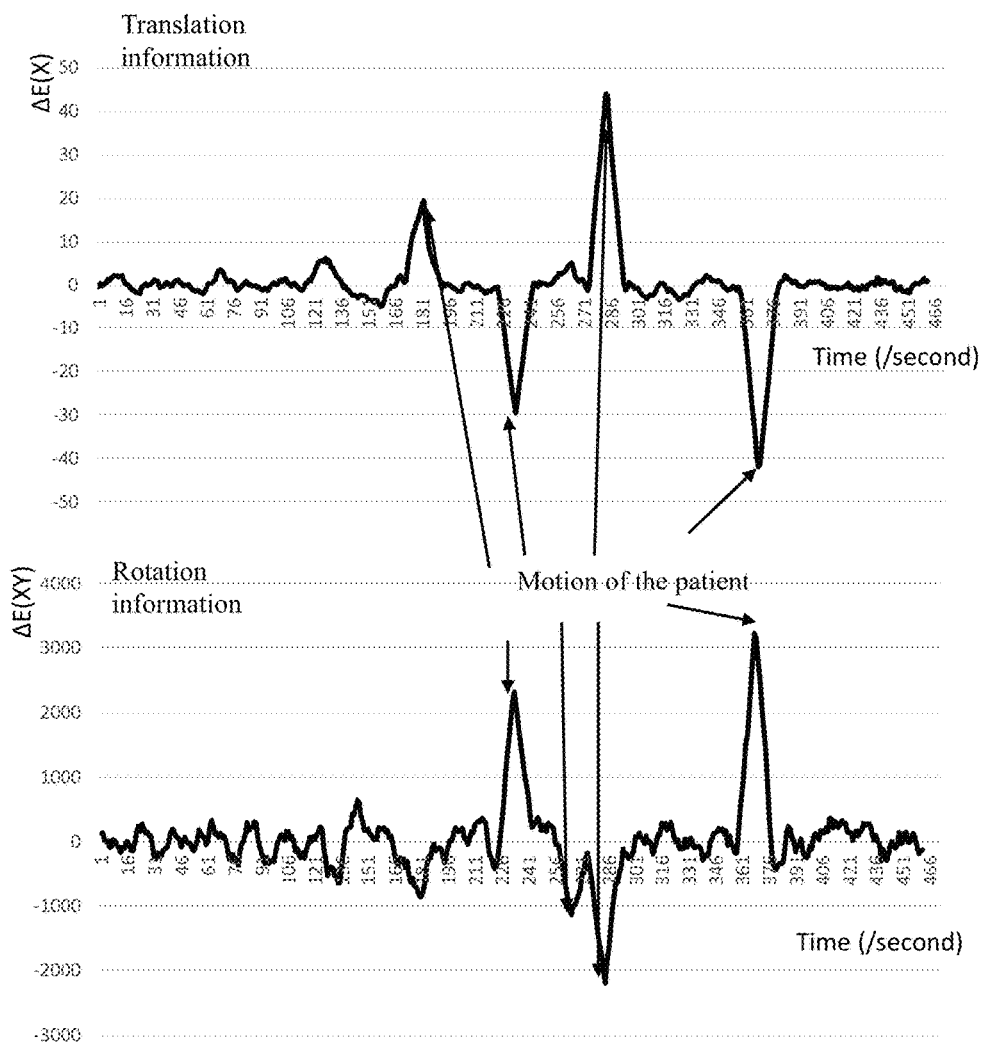
FIG. 23 provides an example of motion detection based on translation information and rotation information according to some embodiments of the present disclosure.

FIG. 23 provides an example of motion detection based on translation information and rotation information according to some embodiments of the present disclosure. As illustrated in FIG. 23, motion may be detected based on the gradient of translation information ($\Delta E(X)$) and the gradient value of rotation information ($\Delta E(XY)$). The arrow indicates the position where the subject may undergo some rigid motion, such as translation and/or rotation.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, microcode, etc.) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the operator's computer, partly on the operator's computer, as a stand-alone software package, partly on the operator's computer and partly on a remote computer or entirely on the remote computer or server. In the latter scenario, the remote computer may be connected to the operator's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

What is claimed is:

1. A method implemented on at least one machine each of which has at least one processor and storage, the method comprising:
    acquiring list mode data relating to a subject;
    dividing the list mode data based on time information and/or spatial information;
    establishing a relationship between data-space and reconstruction space;
    obtaining, based on the divided list mode data and the relationship, expectation information of rigid motion of subject without performing image reconstruction; and
    determining, based on the expectation information, translation information and rotational information to detect the rigid motion of the subject.

2. The method of claim 1, further comprising
    detecting the rigid motion of the subject based on the translation information and the rotational information.

3. The method of claim 2, wherein the detection of the rigid motion is based on a threshold.

4. The method of claim 2, wherein the detection of the rigid motion is performed in an automatic way.

5. The method of claim 1, the dividing the list mode data comprising
    gating the list mode data based on the translation information and the rotational information.

6. The method of claim 5, wherein the gating of the divided list mode data is based on a threshold.

7. The method of claim 1, further comprising
    correcting the divided list mode data with respect to the rigid motion of the subject.

8. The method of claim 7, the correcting the divided list mode data comprising
    performing the correcting in an in situ way.

9. A system, comprising:
    one or more storage devices comprising a set of instructions; and
    one or more processors configured to communicate with the one or more storage devices, wherein when executing the set of instructions, the one or more processors are configured to cause the system to:
        acquire list mode data relating to a subject;
        divide the list mode data based on time information and/or spatial information;
        establish a relationship between data-space and reconstruction space;
        obtain, based on the divided list mode data and the relationship, expectation information of rigid motion of subject without performing image reconstruction; and
        determine, based on the expectation information, translation information and rotational information to detect the rigid motion of the subject.

10. The system of claim 9, wherein the one or more processors are further configured to cause the system to:
    detect the rigid motion of the subject based on the translation information and the rotational information.

11. The system of claim 10, wherein the detection of the rigid motion is based on a threshold.

12. The system of claim 10, wherein the detection of the rigid motion is performed in an automatic way.

13. The system of claim 9, wherein to divide the list mode data, the one or more processors are configured to cause the system to:
    gate the list mode data based on the translation information and the rotational information.

14. The system of claim 13, wherein the gating of the divided list mode data is based on a threshold.

15. The system of claim 9, wherein the one or more processors are further configured to cause the system to:
    correct the divided list mode data from the rigid motion of the subject.

16. The system of claim 15, wherein to correct the divided list mode data, the one or more processors are configured to cause the system to:
    perform the correcting in an in situ way.

17. A non-transitory computer readable medium, comprising at least one set of instructions, wherein when executed by one or more processors of a computing device, the at least one set of instructions causes the computing device to perform a method, the method comprising:
    acquiring list mode data relating to a subject;
    dividing the list mode data based on time information and/or spatial information;
    establishing a relationship between data-space and reconstruction space;
    obtaining, based on the divided list mode data and the relationship, expectation information of rigid motion of subject without performing image reconstruction; and
    determining, based on the expectation information, translation information and rotational information to detect the rigid motion of the subject.

18. The non-transitory computer readable medium of claim 17, the method further comprising
    detecting the rigid motion of the subject based on the translation information and the rotational information.

19. The non-transitory computer readable medium of claim 18, wherein the detection of the rigid motion is based on a threshold.

20. The non-transitory computer readable medium of claim 18, wherein the detection of the rigid motion is performed in an automatic way.

* * * * *